(12) United States Patent
Wiederkehr et al.

(10) Patent No.: US 10,499,968 B2
(45) Date of Patent: Dec. 10, 2019

(54) CABLE PLUGS FOR BONE PLATES

(71) Applicant: Stryker European Holdings I, LLC, Kalamazoo, MI (US)

(72) Inventors: Andreas Wiederkehr, Biel/Bienne (CH); Pierre-Luc Sylvestre, Grenchen (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 524 days.

(21) Appl. No.: 14/657,188

(22) Filed: Mar. 13, 2015

(65) Prior Publication Data

US 2016/0038199 A1  Feb. 11, 2016

Related U.S. Application Data

(60) Provisional application No. 62/093,127, filed on Dec. 17, 2014, provisional application No. 62/035,074, filed on Aug. 8, 2014.

(51) Int. Cl.
| | | |
|---|---|---|
| *A61B 17/82* | (2006.01) | |
| *A61B 17/84* | (2006.01) | |
| *A61B 17/88* | (2006.01) | |
| A61B 17/80 | (2006.01) | |

(52) U.S. Cl.
CPC ............ *A61B 17/82* (2013.01); *A61B 17/842* (2013.01); *A61B 17/8861* (2013.01); *A61B 17/80* (2013.01)

(58) Field of Classification Search
CPC ............................. A61B 17/82; A61B 17/842
See application file for complete search history.

(56) References Cited

U.S. PATENT DOCUMENTS

| | | |
|---|---|---|
| 1,025,008 A | 4/1912 | Miner |
| 1,159,863 A | 4/1913 | Park |
| 2,226,393 A | 12/1940 | Seeger et al. |
| 3,534,731 A | 10/1970 | Muller |
| 3,547,114 A | 12/1970 | Haboush |
| 3,596,656 A | 8/1971 | Kaute |
| 3,997,138 A | 12/1976 | Crock et al. |

(Continued)

FOREIGN PATENT DOCUMENTS

| | | |
|---|---|---|
| DE | 202004015582 U1 | 12/2004 |
| EP | 0075225 A2 | 3/1983 |

(Continued)

OTHER PUBLICATIONS

Cable Ready Cable Grip System, Comprehensive Cable Grip System, Zimmer, 2001.

(Continued)

*Primary Examiner* — Olivia C Chang
(74) *Attorney, Agent, or Firm* — Lerner, David, Littenberg, Krumholz & Mentlik, LLP

(57) ABSTRACT

Various embodiments of a cable plug and a cable wire attachment plate are disclosed herein. Each plug or plate has a cable retaining portion and a fastening portion disposed from the cable retaining portion about a longitudinal axis of the plug or plate. Each cable retaining portion preferably has an aperture or channel for receiving a cable wire therein, while each fastening portion is adapted to engage a portion of a bone plate, such as a hole in the bone plate or an exterior surface of the bone plate. Related methods, systems, and kits are also disclosed.

20 Claims, 18 Drawing Sheets

(56) References Cited

U.S. PATENT DOCUMENTS

| | | | |
|---|---|---|---|
| 4,146,022 A | 3/1979 | Johnson et al. |
| 4,388,921 A | 6/1983 | Sutter et al. |
| 4,484,570 A | 11/1984 | Sutter et al. |
| 4,493,317 A | 1/1985 | Klaue |
| 4,641,636 A | 2/1987 | Cotrel |
| 4,692,290 A | 9/1987 | Steele et al. |
| 4,794,918 A | 1/1989 | Wolter |
| 4,828,441 A | 5/1989 | Frasca |
| 4,867,144 A | 9/1989 | Karas et al. |
| 4,946,458 A | 8/1990 | Harms et al. |
| 4,964,403 A | 10/1990 | Karas et al. |
| 5,013,313 A | 5/1991 | Surer |
| 5,041,113 A | 8/1991 | Biedermann et al. |
| 5,053,036 A | 10/1991 | Perren et al. |
| 5,057,111 A | 10/1991 | Park |
| 5,090,854 A | 2/1992 | Hafeli et al. |
| 5,108,399 A | 4/1992 | Eitenmuller et al. |
| 5,127,914 A | 7/1992 | Calderale et al. |
| 5,129,899 A | 7/1992 | Small et al. |
| 5,147,363 A | 9/1992 | Harle |
| 5,151,103 A | 9/1992 | Tepic et al. |
| 5,190,545 A | 3/1993 | Corsi et al. |
| 5,209,751 A | 5/1993 | Farris et al. |
| 5,234,431 A | 8/1993 | Keller |
| 5,269,784 A | 12/1993 | Mast |
| 5,415,658 A | 5/1995 | Kilpela et al. |
| 5,536,268 A | 7/1996 | Griss |
| 5,549,608 A | 8/1996 | Errico et al. |
| 5,554,157 A | 9/1996 | Errico et al. |
| 5,584,834 A | 12/1996 | Errico et al. |
| 5,586,984 A | 12/1996 | Errico et al. |
| 5,607,430 A | 3/1997 | Bailey |
| 5,618,144 A | 4/1997 | Leistner |
| 5,643,261 A | 7/1997 | Schafer et al. |
| 5,647,873 A | 7/1997 | Errico et al. |
| 5,649,927 A | 7/1997 | Kilpela et al. |
| 5,658,285 A | 8/1997 | Marnay et al. |
| 5,665,089 A | 9/1997 | Dall et al. |
| 5,669,911 A | 9/1997 | Errico et al. |
| 5,690,630 A | 11/1997 | Errico et al. |
| 5,702,393 A | 12/1997 | Pfaifer |
| 5,702,399 A | 12/1997 | Kilpela et al. |
| 5,741,259 A | 4/1998 | Chan |
| 5,810,823 A | 9/1998 | Klaue et al. |
| 5,810,824 A | 9/1998 | Chan |
| 5,817,094 A | 10/1998 | Errico et al. |
| 5,891,145 A | 4/1999 | Morrison et al. |
| 5,910,142 A | 6/1999 | Tatar |
| 5,935,133 A | 8/1999 | Wagner et al. |
| 5,938,663 A * | 8/1999 | Petreto ............... A61B 17/7041 606/278 |
| 5,976,141 A | 11/1999 | Haag et al. |
| 6,010,503 A | 1/2000 | Richelsoph et al. |
| 6,149,653 A | 11/2000 | Deslauriers |
| 6,224,598 B1 | 5/2001 | Jackson |
| 6,241,731 B1 | 6/2001 | Fiz et al. |
| 6,440,136 B1 | 8/2002 | Gambale et al. |
| 6,451,021 B1 | 9/2002 | Ralph et al. |
| 6,454,772 B1 | 9/2002 | Jackson |
| 6,485,491 B1 | 11/2002 | Farris et al. |
| 6,520,965 B2 | 2/2003 | Chervitz et al. |
| 6,524,315 B1 * | 2/2003 | Selvitelli ............ A61B 17/7044 606/278 |
| 6,540,748 B2 | 4/2003 | Lombardo |
| 6,540,749 B2 | 4/2003 | Schafer et al. |
| 6,547,790 B2 | 4/2003 | Harkey, III et al. |
| 6,554,834 B1 | 4/2003 | Crozet et al. |
| 6,575,975 B2 | 6/2003 | Brace et al. |
| 6,585,739 B2 | 7/2003 | Kuras et al. |
| 6,652,526 B1 | 11/2003 | Arafiles |
| 6,660,004 B2 | 12/2003 | Barker et al. |
| 6,663,635 B2 | 12/2003 | Frigg et al. |
| 6,668,688 B2 | 12/2003 | Zhao et al. |
| 6,669,700 B1 | 12/2003 | Farris et al. |
| 6,682,533 B1 | 1/2004 | Dinsdale et al. |
| 6,689,136 B2 | 2/2004 | Stoffella |
| 6,730,093 B2 | 5/2004 | Saint Martin |
| 6,755,829 B1 | 6/2004 | Bono et al. |
| 6,786,903 B2 | 9/2004 | Lin |
| 6,918,912 B2 | 7/2005 | Seemann |
| 6,960,213 B2 | 11/2005 | Chervitz et al. |
| 6,964,666 B2 | 11/2005 | Jackson |
| 7,001,387 B2 | 2/2006 | Farris et al. |
| 7,018,378 B2 | 3/2006 | Biedermann et al. |
| 7,081,116 B1 | 7/2006 | Carly |
| 7,081,117 B2 | 7/2006 | Bono et al. |
| D536,453 S | 2/2007 | Young et al. |
| 7,204,837 B2 | 4/2007 | Paul |
| 7,250,054 B2 | 7/2007 | Allen et al. |
| 7,252,670 B2 | 8/2007 | Morrison et al. |
| 7,255,699 B2 | 8/2007 | Paul |
| 7,276,070 B2 | 10/2007 | Muckter |
| 7,278,997 B1 | 10/2007 | Mueller et al. |
| 7,320,556 B2 | 1/2008 | Vagn-Erik |
| 7,341,589 B2 | 3/2008 | Weaver et al. |
| 7,407,504 B2 | 8/2008 | Dongar et al. |
| 7,513,905 B2 | 4/2009 | Jackson |
| 7,530,992 B2 | 5/2009 | Biedermann et al. |
| 7,588,575 B2 | 9/2009 | Colleran et al. |
| 7,604,655 B2 | 10/2009 | Warnick |
| 7,618,444 B2 | 11/2009 | Shluzas |
| 7,625,394 B2 | 12/2009 | Molz, IV et al. |
| 7,641,676 B2 | 1/2010 | Mathieu et al. |
| 7,645,294 B2 | 1/2010 | Kalfas et al. |
| 7,655,009 B2 | 2/2010 | Grusin |
| 7,662,172 B2 | 2/2010 | Warnick |
| 7,662,175 B2 | 2/2010 | Jackson |
| 7,666,185 B2 | 2/2010 | Ryan et al. |
| 7,686,834 B2 | 3/2010 | Saint Martin |
| 7,686,835 B2 | 3/2010 | Warnick |
| 7,691,133 B2 | 4/2010 | Partin et al. |
| 7,695,472 B2 | 4/2010 | Young |
| 7,704,271 B2 | 4/2010 | Abdou |
| 7,708,762 B2 | 5/2010 | McCarthy et al. |
| 7,722,651 B2 | 5/2010 | Kwak et al. |
| 7,722,653 B2 | 5/2010 | Young et al. |
| 7,731,735 B2 | 6/2010 | Morrison |
| 7,740,648 B2 | 6/2010 | Young et al. |
| 7,740,649 B2 | 6/2010 | Mosca et al. |
| 7,766,911 B1 | 8/2010 | Navarro et al. |
| 7,766,917 B2 | 8/2010 | Kugler et al. |
| 7,771,458 B2 | 8/2010 | Biedermann et al. |
| 7,780,666 B1 | 8/2010 | Navarro et al. |
| 7,785,327 B1 | 8/2010 | Navarro et al. |
| 7,785,356 B2 | 8/2010 | Biedermann et al. |
| 7,789,900 B2 | 9/2010 | Levy et al. |
| 7,828,826 B2 | 11/2010 | Drewry et al. |
| 7,828,829 B2 | 11/2010 | Ensign |
| 7,833,226 B2 | 11/2010 | Grabowski et al. |
| 7,833,256 B2 | 11/2010 | Biedermann et al. |
| 7,850,717 B2 | 12/2010 | Dewey et al. |
| 7,857,839 B2 | 12/2010 | Duong et al. |
| 7,892,259 B2 | 2/2011 | Biedermann et al. |
| 7,905,883 B2 | 3/2011 | Bruecker et al. |
| 7,905,910 B2 | 3/2011 | Gerlach et al. |
| 7,909,855 B2 | 3/2011 | Drewry et al. |
| 7,909,858 B2 | 3/2011 | Gerlach et al. |
| 7,909,859 B2 | 3/2011 | Mosca et al. |
| 7,909,860 B2 | 3/2011 | Rathbun et al. |
| 7,922,748 B2 | 4/2011 | Hoffman |
| 7,938,829 B2 | 5/2011 | Mullaney |
| 7,942,910 B2 | 5/2011 | Doubler et al. |
| 7,942,911 B2 | 5/2011 | Doubler et al. |
| 7,947,064 B2 | 5/2011 | Bergeron et al. |
| 7,951,172 B2 | 5/2011 | Chao et al. |
| 7,967,849 B2 | 6/2011 | Carson et al. |
| 7,967,851 B2 | 6/2011 | Bickley et al. |
| 7,988,711 B2 | 8/2011 | Erickson et al. |
| 8,002,806 B2 | 8/2011 | Justis |
| 8,012,185 B2 | 9/2011 | Warnick |
| 8,012,186 B2 | 9/2011 | Pham et al. |
| 8,016,866 B2 | 9/2011 | Warnick |
| 8,025,683 B2 | 9/2011 | Morrison |
| 8,048,124 B2 | 11/2011 | Chin et al. |

(56) References Cited

U.S. PATENT DOCUMENTS

| | | |
|---|---|---|
| 8,048,131 B2 | 11/2011 | Dalton |
| 8,048,132 B2 | 11/2011 | Wu et al. |
| 8,052,724 B2 | 11/2011 | Jackson |
| 8,075,599 B2 | 12/2011 | Johnson et al. |
| 8,080,010 B2 | 12/2011 | Schulz et al. |
| 8,080,040 B2 | 12/2011 | Miller |
| 8,083,776 B2 | 12/2011 | Alvarez |
| 8,083,777 B2 | 12/2011 | Butters et al. |
| 8,092,504 B2 | 1/2012 | Warnick |
| 8,105,367 B2 | 1/2012 | Austin et al. |
| 8,114,140 B2 | 2/2012 | Derouet |
| 8,133,262 B2 | 3/2012 | Whipple |
| 8,142,434 B2 | 3/2012 | Bluechel |
| 8,142,481 B2 | 3/2012 | Warnick |
| 8,142,483 B2 | 3/2012 | Drewry et al. |
| 8,147,493 B2 | 4/2012 | Dutoit et al. |
| 8,147,522 B2 | 4/2012 | Warnick |
| 8,167,910 B2 | 5/2012 | Nilsson |
| 8,177,816 B2 | 5/2012 | Schwab |
| 8,177,823 B2 | 5/2012 | Lake et al. |
| 8,192,470 B2 | 6/2012 | Biedermann et al. |
| 8,343,155 B2 | 1/2013 | Fisher et al. |
| 8,398,690 B2 | 3/2013 | Bottlang et al. |
| 2002/0128654 A1 | 9/2002 | Steger et al. |
| 2003/0187434 A1 | 10/2003 | Lin |
| 2004/0138666 A1 | 7/2004 | Molz et al. |
| 2005/0038428 A1 | 2/2005 | Kelman et al. |
| 2005/0234467 A1 | 10/2005 | Rains |
| 2006/0111715 A1 | 5/2006 | Jackson |
| 2006/0195093 A1 | 8/2006 | Jahng |
| 2006/0217713 A1 | 9/2006 | Serhan et al. |
| 2006/0217714 A1 | 9/2006 | Serhan et al. |
| 2006/0217715 A1 | 9/2006 | Serhan et al. |
| 2006/0235393 A1 | 10/2006 | Bono et al. |
| 2007/0293861 A1* | 12/2007 | Rezach ............... A61B 17/7037 606/60 |
| 2008/0015591 A1 | 1/2008 | Castaneda et al. |
| 2008/0097448 A1 | 4/2008 | Binder et al. |
| 2008/0300599 A1 | 12/2008 | Anapliotis et al. |
| 2009/0204151 A1 | 8/2009 | Bracken |
| 2009/0248077 A1 | 10/2009 | Johns |
| 2009/0287215 A1* | 11/2009 | Fisher ................... A61B 17/80 606/71 |
| 2009/0287255 A1 | 11/2009 | Erickson et al. |
| 2010/0234896 A1 | 9/2010 | Lorenz et al. |
| 2011/0130792 A1 | 6/2011 | Nydegger et al. |
| 2013/0053894 A1 | 2/2013 | Gamache et al. |
| 2014/0052189 A1* | 2/2014 | Hammer ............ A61B 17/7032 606/278 |

FOREIGN PATENT DOCUMENTS

| | | |
|---|---|---|
| EP | 0600938 A1 | 6/1994 |
| EP | 0791338 A2 | 8/1997 |
| EP | 0791338 B1 | 8/2003 |
| EP | 1075225 B1 | 12/2004 |
| WO | 9909904 A1 | 3/1999 |
| WO | 2004107996 A1 | 12/2004 |

OTHER PUBLICATIONS

Cable-Ready Greater Trochanteric Reattachment, Surgical Technique, Zimmer, 2001, 2008, 2010.
Howmedica Osteonics, Dall-Miles Cable System, 2000.
Extended European Search Report for Application No. EP15002307 dated Dec. 15, 2015.

* cited by examiner

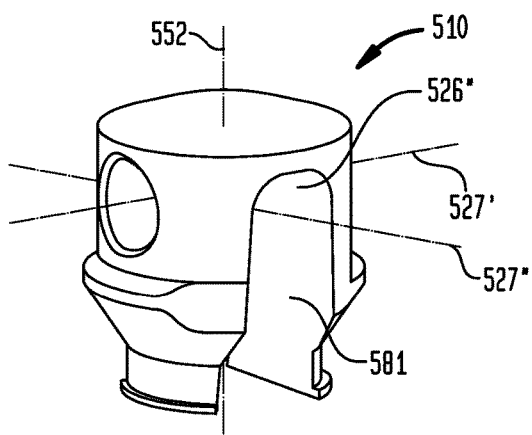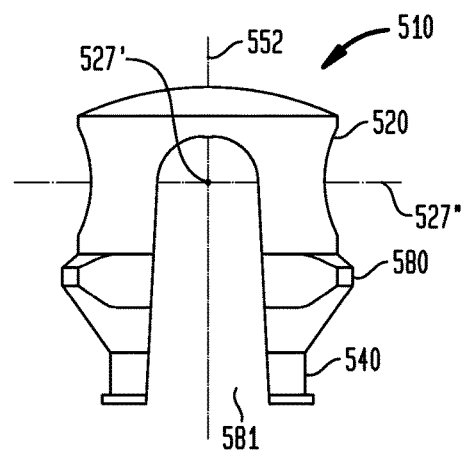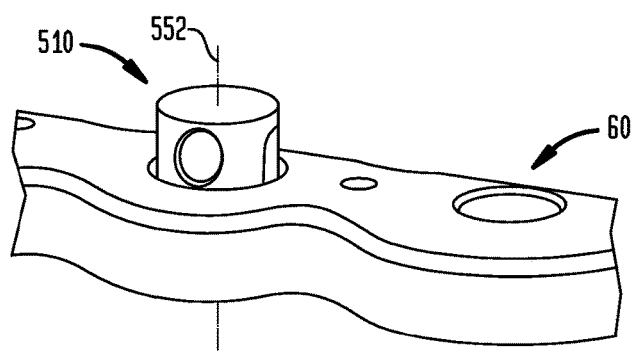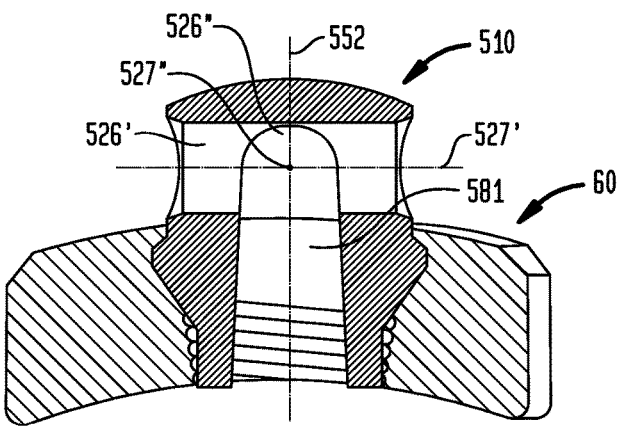

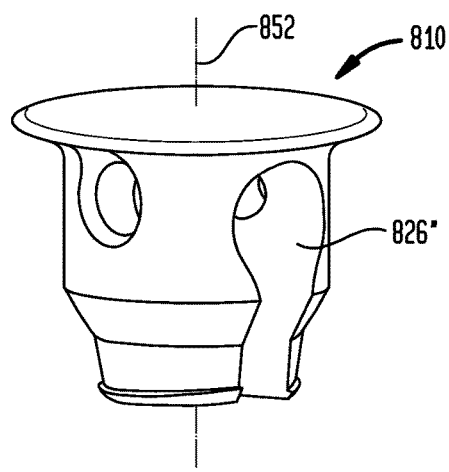
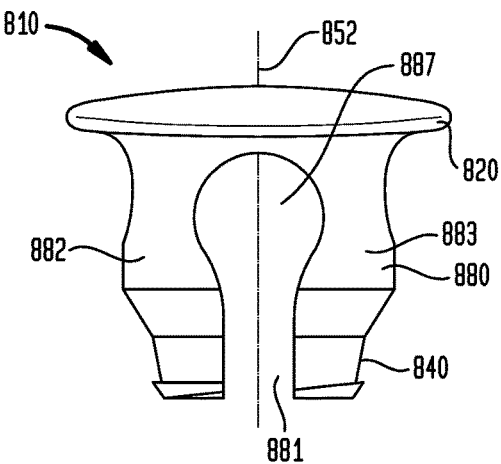
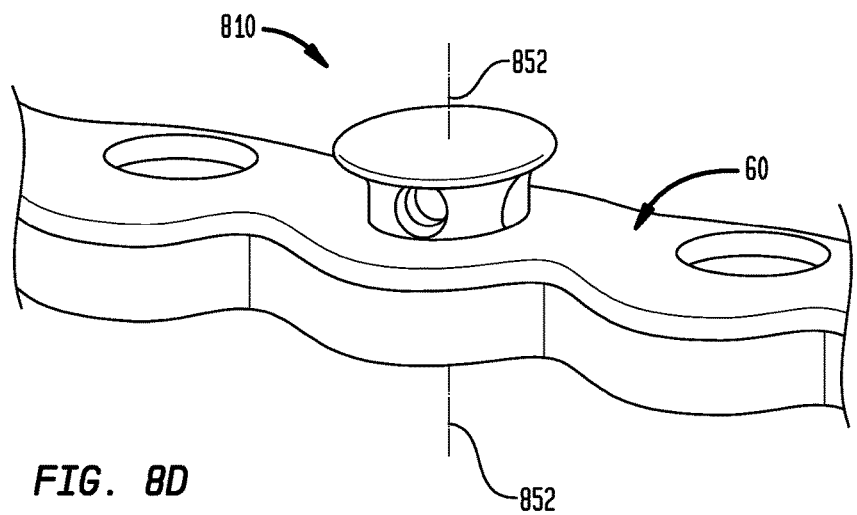
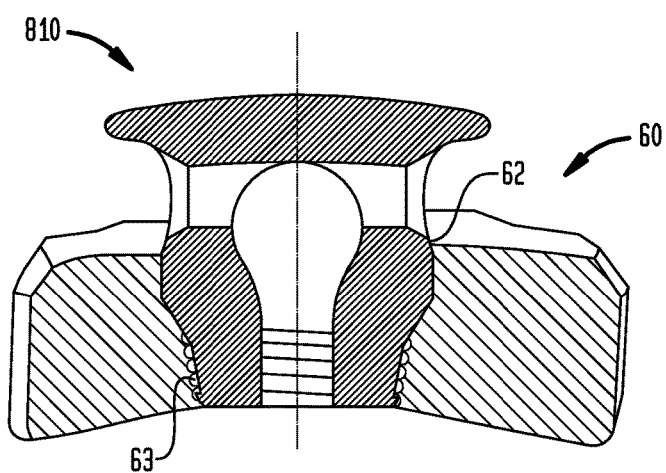

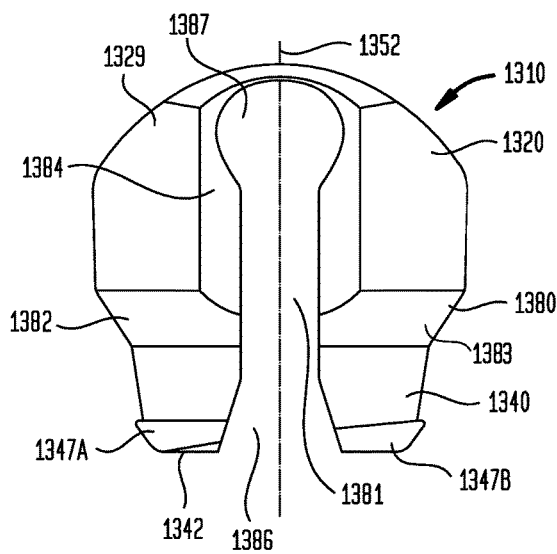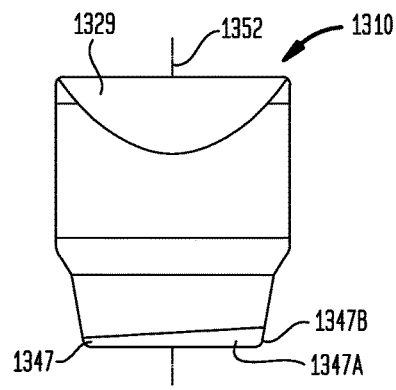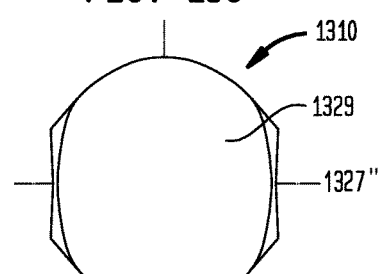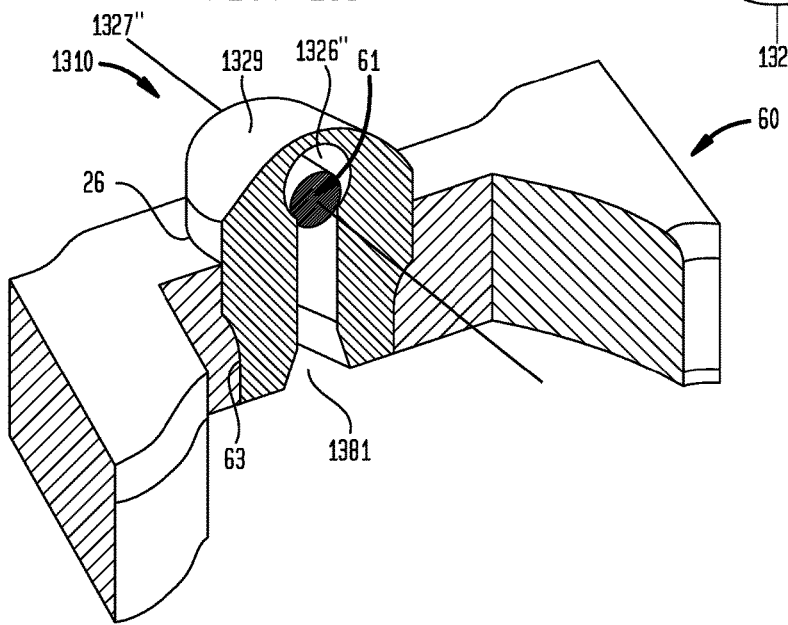

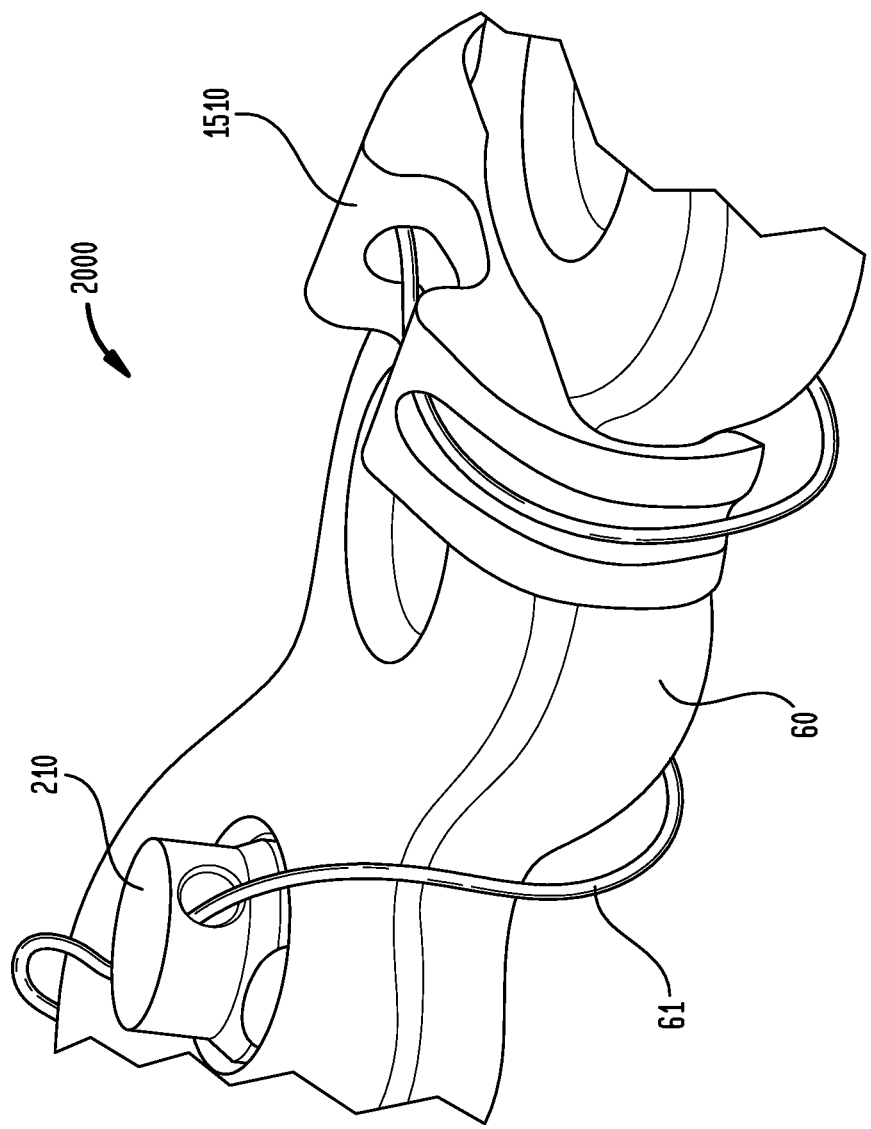

CABLE PLUGS FOR BONE PLATES

CROSS-REFERENCE TO RELATED APPLICATIONS

The present application claims priority from provisional U.S. Patent Application Ser. No. 62/093,127, filed Dec. 17, 2014, and provisional U.S. Patent Application Ser. No. 62/035,074, filed Aug. 8, 2014, both of which are incorporated herein by reference.

FIELD OF THE INVENTION

The present invention relates to systems for coupling surgical cables to bone plates when reducing bone fractures or repairing fractured bones. More particularly, the invention relates to systems that utilize a cable plug or a cable attachment plate, affixed to a bone plate, to receive and retain a surgical cable. In some embodiments, the surgical cable may be oriented with respect to the bone at a plurality of angles relative to the longitudinal axis of the bone.

BACKGROUND OF THE INVENTION

Surgical cables are used in many surgical procedures. They are generally used to encircle the bone alone, or the bone and a bone plate, to facilitate fixation of one or more bone fragments. Some bone fixation systems that use surgical cable also use a bone plate having a length sufficient to span the bone fragments, fixation screws to couple the bone plate to the bone, adapters to couple the cable to the bone plate, and crimp devices for securing ends of the cable. In these systems, the surgical cable is generally coupled to the bone or the bone plate at 90° from the longitudinal axis of the bone.

Because the surgical cable is wrapped around the bone and bone plate, as forces act on the cable, the cable may tend to move from its coupled position with respect to the bone plate. As such forces act on the cable, a longitudinal axis of the cable will generally tend to be angled at less than 90° from the longitudinal axis of the bone. This may result in shear stresses and strains in the surgical cable that cause the bone plate to shift relative to the bone.

Some fixation screws function to both couple the bone plate to bone and serve as a means for coupling the cable at a certain position along a length of the bone plate. If the fixation screws are used to couple the cable to the bone plate, then the cable is generally received in a slot or bore in a head portion of the fixation screws. Such fixation screws also act as an adapter. The head portion of the fixation screws are generally integrally coupled to a shaft of the fixation screws but may be a separate component that is coupled to the shaft of the fixation screws.

The adapters and fixation screws explained above generally function to prevent migration of surgical cable along a longitudinal axis of a bone plate. These systems do not, however, provide a means of orienting the surgical cable at an angle less than 90° from the longitudinal axis of the bone. Therefore, they cannot sufficiently eliminate the stresses and strains in the surgical cable which may cause shifting of the bone plate.

BRIEF SUMMARY OF THE INVENTION

A first aspect of the present invention is a cable plug with a cable retaining portion and fastening portion. The cable retaining portion preferably has at least one passage for receiving a cable wire therethrough. The fastening portion is disposed from the cable retaining portion about a longitudinal axis of the cable plug. Desirably, the fastening portion has a first sidewall and a second sidewall opposite of the first sidewall along a first lateral axis transverse with the longitudinal axis. In accordance with this first aspect, the first and second sidewalls may define an interior conduit that extends through the cable plug along a second lateral axis transverse to the first lateral axis. The passage may form at least a portion of the interior conduit. Likewise, the passage may have a profile corresponding to the profile of the cable wire, such as bulbous profile.

An aperture may extend through the cable retaining portion along the first lateral axis to receive a cable wire therethrough. A portion of the interior conduit may intersect or be in communication with the aperture. Preferably still, each of the first and second sidewalls is biased away from the longitudinal axis to facilitate engagement of the cable plug with a bone plate. These features enhance the flexibility and resiliency of the cable plug.

Any cable plug in accord with this first aspect may have top surface with a portion that is convexly shaped. The cable retaining portion may alternatively have a top surface with a first diameter and a side surface with a second diameter, the first diameter being larger than the second diameter. This first aspect may further comprise at least one cable retaining arm that extends outwardly from a surface of the cable retaining portion, such as the top surface, along the first lateral axis. Each cable retaining arm desirably has an aperture for receiving a surgical cable therethrough. Each aperture may be substantially circular or semi-circular.

Preferably, the fastening portion is disposed from the cable retaining portion about a longitudinal axis of the cable plug. The fastening portion may comprise a first sidewall and a second sidewall. The second sidewall is desirably opposite of the first sidewall along a first lateral axis transverse with the longitudinal axis. This allows the first and second sidewalls to define an interior conduit that extends through the cable plug along a second lateral axis transverse to the first lateral axis. A passage for receiving a cable wire forms at least a portion of the interior conduit. An alternate fastening portion may comprise a pair of first and second biased legs. Similar to above, the legs may form an interior conduit that extends through the cable plug along an axis transverse to the longitudinal axis. Each of the first and second biased legs desirably has a protrusion extending outwardly from an outer surface thereof. As before, the passage described above may form at least a portion of the interior conduit. Each portion of protrusion extending from the first and second biased legs may form a portion of a thread adapted to engage an aperture in the bone plate. Each of the first and second biased legs has an inner sidewall opposite the outer surfaces thereof. Each inner sidewall of the first and second biased legs is desirably separated by a length that is less than a diameter of the passage.

Any cable plug describe herein may also be described as having an intermediate portion disposed between the cable retaining portion and the fastening portion along a longitudinal axis of the cable plug. The intermediate portion preferably has a first sidewall and a second sidewall opposite of the first sidewall along a first lateral axis transverse with the longitudinal axis. This allows the interior conduit to be formed between the cable retaining portion, the first and second sidewalls of the intermediate portion, and the fastening portion. As before, the passage desirably forms at least a portion of the interior conduit. An aperture may extend through the cable retaining portion along the first lateral axis. The aperture is preferably intersects or is in communication with the passage. In some instances, the interior conduit may be enclosed within the intermediate portion. The conduit may have an oblong shaped opening. This allows either the first or second sidewall may flex in response to a force applied to the cable plug.

Yet another cable plug in accordance with this first aspect may have a "V" shaped profile. This cable plug desirably has a cable retaining portion with a first sidewall and a second sidewall opposite of the first sidewall along a first lateral axis transverse with a longitudinal axis of the cable plug. At least one cable retaining arm preferably extends from either of the first or second sidewalls along the first lateral axis. Preferably still, at least one aperture for receiving a cable wire is integral with each of the at least one cable retaining arms. The fastening portion of this cable plug is also disposed from the cable retaining portion about the longitudinal axis. To form the "V" shape, each of the first and second sidewalls of the cable retaining portion extends from the fastening portion to form an interior conduit. Preferably, this conduit extends along a second lateral axis transverse to the first lateral axis. Each of the first and second sidewalls may also have a protrusion extending outwardly therefrom.

A second aspect of the present invention is a cable attachment plate comprising a cable retaining portion and a fastening portion. The cable retaining portion has a first channel for receiving a cable wire therein. This first channel desirably runs along at least a portion of the attachment plate. As before, the fastening portion is preferably disposed from the cable retaining portion about a longitudinal axis of the attachment plate. The fastening portion may have a pair of first and second sidewalls that flex relative to the longitudinal axis. At least a portion of each of the first and second sidewalls is desirably adapted to contact the bone plate. The first and second sidewalls may be biased towards one another. To enhance the biasing force, a resilient section of the attachment plate may be adapted to bias the first and second sidewalls towards one another. The first channel described above may be at least partially defined by at least two cable receiving members extending upward from a base surface of the cable retaining portion.

The first channel may include at least one closed portion forming an aperture for receiving the cable wire. The dimensions of the first channel may vary. For example, the cable wire may have a cable diameter and the at least two projections of the cable retaining portion may be separated by a width slightly less than the cable diameter, each projection being adapted to receive the wire therebetween. Alternatively, the at least two cable receiving members may be separated by a width equal to or greater than the cable diameter. Any first channel in accordance with this second aspect may wrap around the cable retaining portion and at least a portion of each of the first and second sidewalls. The cable retaining portion may also include a second channel with at least one portion that is transverse with or parallel to the first channel.

A cable attachment plate of this second aspect may be adapted to have a bone plate contact surface. For example, a bone plate contact surface may be formed by an underside of the cable retaining portion and an interior surface of each of the first and second sidewalls. This surface preferably has at least one protrusion extending outwardly therefrom to establish a point of contact with the exterior surface of the bone plate. Multiple protrusions may be used. As further example, the at least one protrusion may alternatively comprise a pair of first protrusions and a pair of second protrusions, each protrusion extending outwardly as before. This establishes four points of contact with the exterior surface of the bone plate.

A portion of the bone plate contact surface may conform to the exterior surface of the bone plate when a compressive force is applied to the cable retaining portion by the cable wire. Preferably, a contact anchor extends outwardly from each end portion of the bone plate contact surface to contact the exterior surface of the bone plate. Each contact anchor may have unique cross-section, such as a triangular cross-section or a rectangular cross-section.

A third aspect of the present invention is directed to a series of methods for securing a bone plate to a bone. These methods may be modified incorporate the structure of any of the cable plugs or cable attachment plates described above. An exemplary method of securing the bone plate to the bone may include the steps engaging a cable plug with an aperture of the bone plate and contacting the bone plate with a bone. A surgical cable having a longitudinal axis may then be wrapped around the bone and received within the cable retaining portion of the cable plug. Once received, the cable wire may be tightened and then fastened to secure the bone plate to the bone of the patient. These method steps may be further modified. For example, if the cable retaining portion of the cable plug has a channel or aperture, then the receiving step may allow the cable wire to be received in either or both of the channel or the aperture. As a further example, the cable wire may also be wrapped a plurality of times so that a first portion of the cable plug is received in the channel and a second portion is received in the aperture.

In other methods according to this third aspect, the cable wire is wrapped around the bone and the bone plate so that a portion of the cable wire is adjacent an aperture of the bone plate. Once positioned, a first and second sidewall of the cable plug may be located on either side of the cable wire. The fastening portion of the cable plug may then be engaged with the aperture in the bone plate. This causes the cable wire to be received within an interior conduit of the cable plug formed by the first and second sidewalls. Preferably, the cable wire is received within a passage that is part of the interior conduit. Once received, the cable wire may be tightened and then fastened to secure the bone plate to the bone of the patient. As before, this method may be modified to match the structure of the cable plug. For example, if the cable plug has an aperture, then the cable wire may also be received within the aperture before being tightened or fastened.

Still other methods are utilized to secure the bone plate to the bone using a cable attachment plate. Such methods may include the steps of placing a bone plate contact surface of an attachment plate in contact with a bone plate and positioning the bone plate adjacent a bone. Once positioned, the cable wire may be received within a cable retaining portion of the attachment plate and wrapped around the bone and the bone plate. This allows the cable wire to be tightened and then fastened to secure the bone plate to the bone. Of course, any of the method steps described above may be combined where a cable plug and a cable attachment plate are used in combination to secure the bone plate to the bone.

A fourth aspect of the present invention is directed to a system comprising any combination of any cable plug or cable attachment plate described herein. This system may include a cable plate, a bone plate, and a cable attachment plate. Similar to above, the cable attachment plate may having a cable retaining portion with at least one channel for receiving the cable wire therein and a fastening portion disposed from the cable retaining portion about a longitudinal axis of the cable attachment plate. The fastening portion preferably has a pair of first and second sidewalls or legs configured to flex relative to the longitudinal axis. The sidewalls or legs may be biased. Preferably still, the cable attachment plate has a bone plate contact surface formed by an underside of the cable retaining portion and an interior surface of each of the first and second sidewalls.

This system allows the cable wire to be secured to the bone plate when the cable wire is received in the cable retaining portion and at least a portion of the bone plate contact surface contacts the exterior surface of the bone plate. This system is not limited to a bone plate of any particular shape. For example, the bone plate may have an undulating perimeter that defines two bulbous portions. A protrusion may extend from the bone plate contact surface. Desirably, the protrusion is adapted to contact a portion of the exterior surfaces of the bone plate that are located between the two bulbous portions. This system may further comprising any cable plug described herein, such as any cable plug have a passage for receiving the cable wire and fastening portion engageable with the bone plate.

A fifth aspect of the present invention includes a kit that comprises any combination of the cable plugs or attachment plates described above. For example, such a kit may comprise a cable wire, a bone plate with at least one aperture, and at least one cable plug engageable with the aperture. Alternatively, such kits may further comprise at least one cable attachment plate engageable with a portion of the bone plate, and any hardware necessary to tighten and fasten the cable wire to secure the bone plate to the bone.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 5A is a perspective view of another embodiment of a cable plug, wherein the cable plug has an interior conduit in the form of a downward facing channel.

FIG. 5B is a profile view of the cable plug shown in FIG. 5A.

FIG. 5C is a perspective view of the cable plug shown in FIG. 5B, wherein the cable plug is engaged with an aperture in the bone plate.

FIG. 5D is a cross-sectional view of the cable plug shown in FIG. 5A.

FIG. 8A is a perspective view of another embodiment of a cable plug, wherein the cable plug has an enlarged top surface and an interior conduit with a bulbous portion.

FIG. 8B is a profile view of the cable plug shown in FIG. 8A.

FIG. 8C is a perspective view of the cable plug shown in FIG. 8B, wherein the cable plug is engaged with an aperture in the bone plate.

FIG. 8D is a cross-sectional view of the cable plug shown in FIG. 8A.

FIG. 13A is a profile view of another embodiment of a cable plug, wherein the cable plug has an interior conduit with a bulbous portion and a chamfered entry portion.

FIG. 13B is a side view of the cable plug shown in FIG. 13A.

FIG. 13C is a top view of the cable plug shown in FIG. 13B.

FIG. 13D is a cross-sectional view of the cable plug shown in FIG. 13A, wherein the cable plug is engaged with an aperture in the bone plate.

FIG. 20 is a perspective view of another exemplary system in accordance with the present invention.

DETAILED DESCRIPTION

Although the embodiments described below and shown in the figures are described with reference to specific embodiments of the present cable plug invention, it is to be understood that the concepts and novelty underlying the present invention could be utilized for any type of medical procedure requiring bone attachment. Moreover, although described in connection with the bone attachment, it is contemplated that the present invention may be used to fix a variety of devices to a variety of surfaces, such as the surface of a synthetic bone or implant.

As used herein, when referring to bones or other parts of the body, the term "proximal" means closer to the heart; "distal" means more distant from the heart; "inferior" means toward the feet; "superior" means towards the head; "anterior" means towards the front part of the body or the face; "posterior" means towards the back of the body; "medial" means toward the midline of the body; and "lateral" means away from the midline of the body.

A series of longitudinal and lateral axes are discussed below. For convenience, these axes might alternatively be described with reference to the terms defined above. For example, some embodiments are described with reference to a longitudinal axis, which might alternatively be described as a superior-inferior axis. Likewise, some embodiments are described with reference to a first lateral axis and a second lateral axis, each of which is transverse with the other and the longitudinal axis. These first and second lateral axes might alternatively be described as, respectfully, an anterior-posterior axis and a medial-lateral axis. Accordingly, a local Cartesian coordinate system is established with respect to a bone and hereby introduced. Of course, because the present invention may be rotated about any equivalent longitudinal axis, or be positioned at any angle relative to either the first or second lateral axis, these descriptors are merely exemplary not intended to limit the present invention to a particular orientation.

Figure 1:
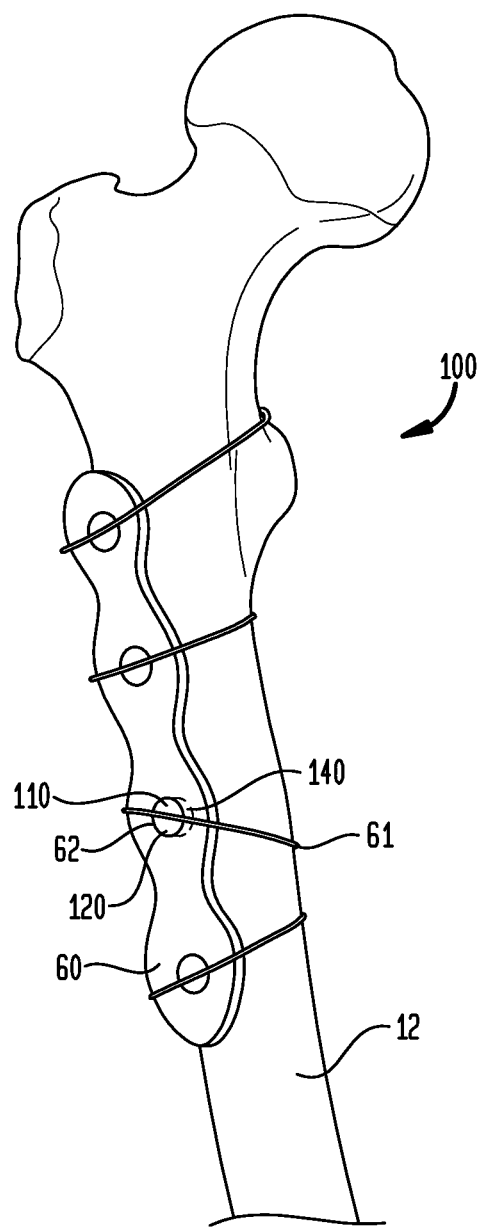
FIG. 1 is a perspective view of one embodiment of a fixation system of the present invention that conceptually shows a cable plug securing a surgical cable to a bone plate.

Referring to FIG. 1, there is shown a bone fixation system 100 engaged to a portion of a femur bone 12. Bone fixation system 100 includes a surgical cable 61 coupled to a bone plate 60 via a cable plug 110. As shown in FIG. 1, a portion of surgical cable 61 is wrapped around femur bone 12 just above the lesser trochanter, while another portion of surgical cable 61 is wrapped around the femoral shaft just below the lower trochanter, and two more portions of surgical cable 61 are wrapped about the femoral shaft some distance below the lesser trochanter. Surgical cable 61 may be embodied as one or more cable wires that are received and retained by one or more cable plugs 110 at a plurality of angles relative to a longitudinal axis of bone 12.

In FIG. 1, each of a plurality of cable plugs 110 is located in an aperture 62 of bone plate 60 such that bottom portion of plug 110 is adjacent femur bone 12. Each cable plug embodiment disclosed in this application preferably has a cable retaining portion and a fastening portion. Referring to FIG. 1, cable plug 110 has a cable retaining portion 120 and a fastening portion 140. Although not shown, cable retaining portion 120 may have a channel or aperture adapted to receive the cable wire. In some embodiments described below, the cable retaining portion 120 has two cable receiving members that project upwardly or downwardly from a base surface of cable plug 110 to form a channel, interior conduit, or passage within the interior conduit. Any cable retaining portion described herein may also have a single cable receiving member. Preferably, each cable receiving member has an outer face adapted to be grasped by the fingers of a user so that cable plug 110 is easily manipulated by hand.

In FIG. 1, cable retaining portion 120 is integral with the fastening portion 140 (conceptually illustrated in dashed lines). An outer circumference of fastening portion 140 may be threaded; in some embodiments, this outer circumference is interrupted by an interior conduit, as noted below. During implantation, cable plug 110 is pressed into aperture 62 of bone plate 60 until a bottom surface of fastening portion 140 is adjacent bone plate 60. This permits rotation of cable plug 110 with respect to bone plate 60 in a first or second direction about a longitudinal axis of cable plug 110. In accordance with this embodiment, surgical cable 61 may be retained within cable retaining portion 120 and oriented a plurality of angles relative to the bone 12.

Numerous cable plug embodiments are disclosed in FIGS. 2A-13D. Where similar components to those of cable plug 110 are included in a cable plug 210, 310, 410, etc., similar reference numerals are utilized, but within that series of numbers. For example, another embodiment of cable plug 110 is depicted in FIGS. 2A-D as a cable plug 210. Similar to above, cable plug 210 has a cable retaining portion 220 integral with a fastening portion 240. Cable plug 210 may also be described as having an intermediate portion 280 located between cable retaining and fastening portions 220 and 240. Desirably, each portion of cable plug 210 is disposed along a longitudinal axis 252 in FIGS. 2A-D. As disclosed with respect to the embodiments set forth below, each portion of the cable plug works to reduce the potential shear stresses and strains that may be transferred to surgical cable 61 by enhancing the flexibility and resiliency of plug 210.

Figure 2A:
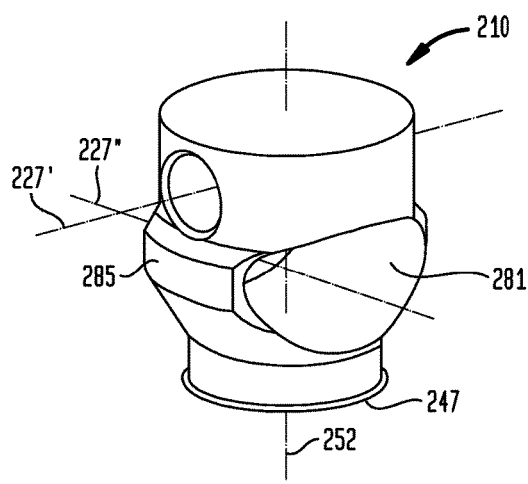
FIG. 2A is a perspective view a cable plug in accordance with the present invention, wherein the cable plug has an aperture and an interior conduit.
Figure 2B:
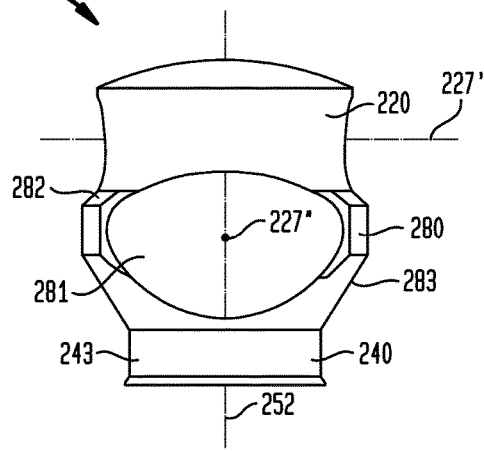
FIG. 2B is a profile view of the cable plug shown in FIG. 2A.
Figure 2C:
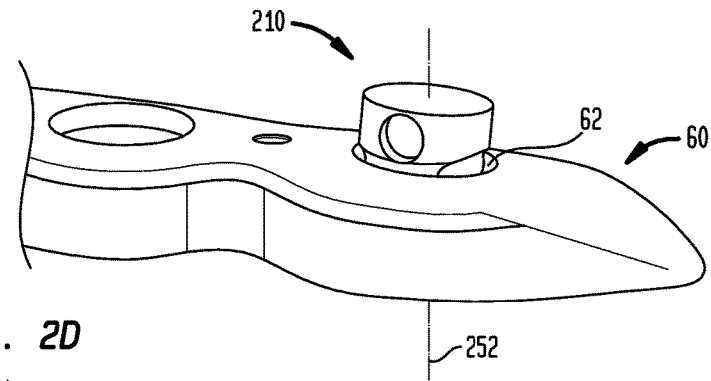
FIG. 2C is a perspective view of the cable plug shown in FIG. 2B, wherein the cable plug is engaged with an aperture in the bone plate.
Figure 2D:
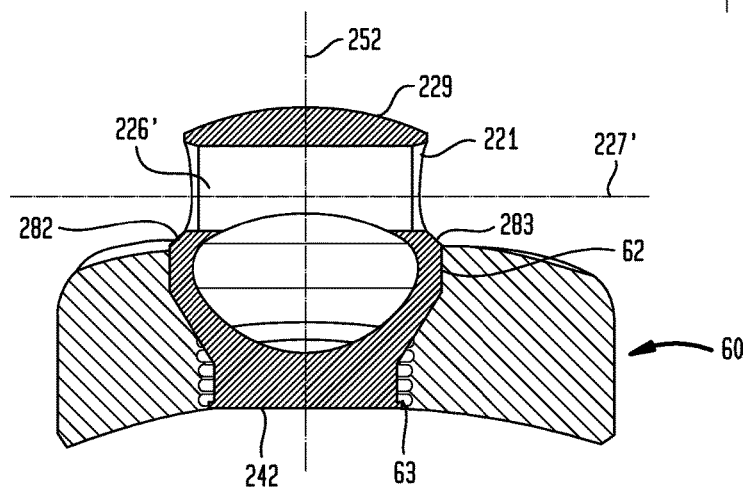
FIG. 2D is a cross-sectional view of the cable plug shown in FIG. 2C.
Figure 3A:
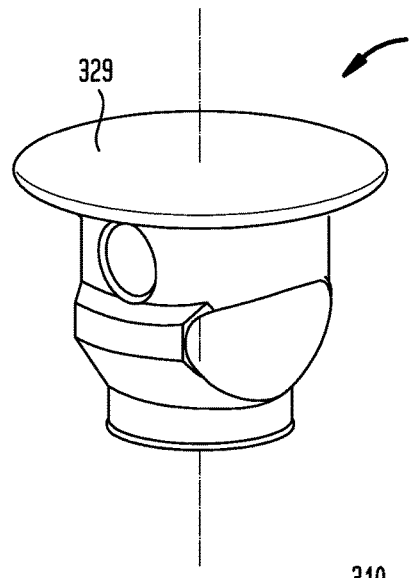
FIG. 3A is a perspective view of another embodiment of a cable plug, wherein the cable plug has an enlarged top surface and an interior conduit.
Figure 3B:
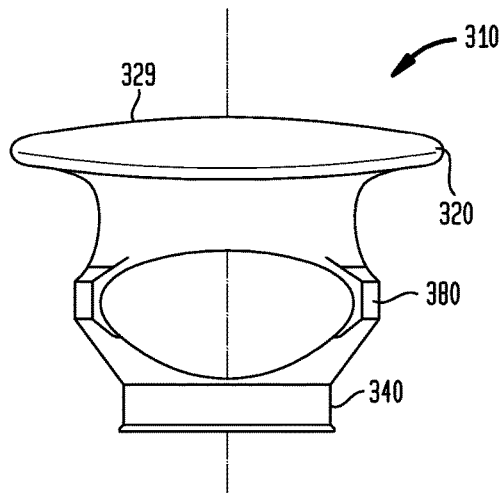
FIG. 3B is a profile view of the cable plug shown in FIG. 3A.
Figure 3C:
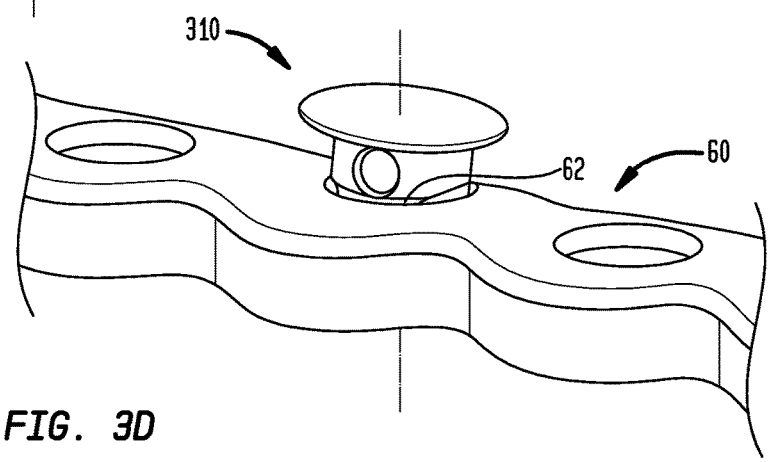
FIG. 3C is a perspective view of the cable plug shown in FIG. 3B, wherein the cable plug is engaged with an aperture in the bone plate.
Figure 3D:
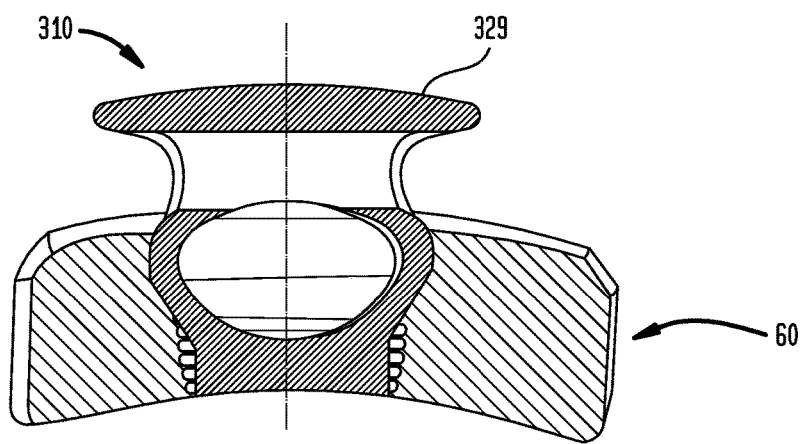
FIG. 3D is a cross-sectional view of the cable plug shown in FIG. 3C.
Figure 4A:
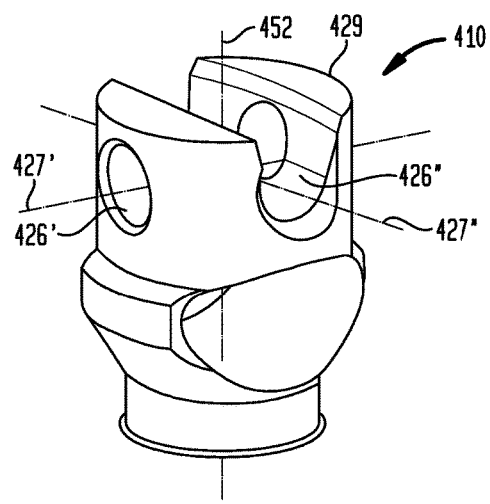
FIG. 4A is a perspective view of another embodiment of a cable plug, wherein the cable plug has an aperture intersected by an upward facing channel.
Figure 4B:
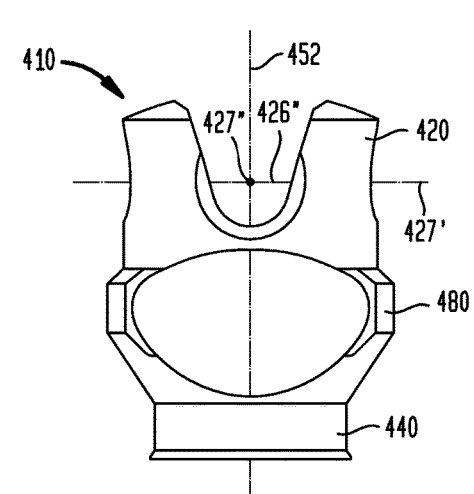
FIG. 4B is a profile view of the cable plug shown in FIG. 4A.
Figure 4C:
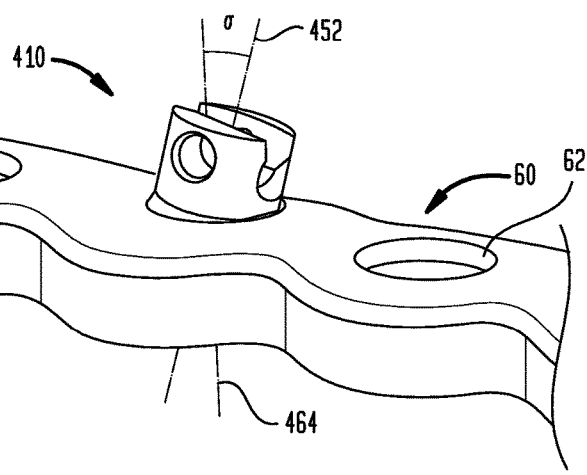
FIG. 4C is a perspective view of the cable plug shown in FIG. 4B, wherein the cable plug is engaged with an aperture in the bone plate and tilted relative thereto.
Figure 4D:
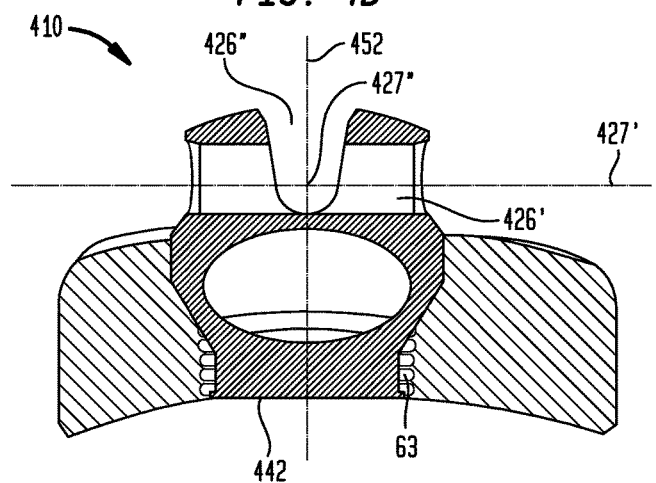
FIG. 4D is a cross-sectional view of the cable plug shown in FIG. 4A.
Figure 6A:
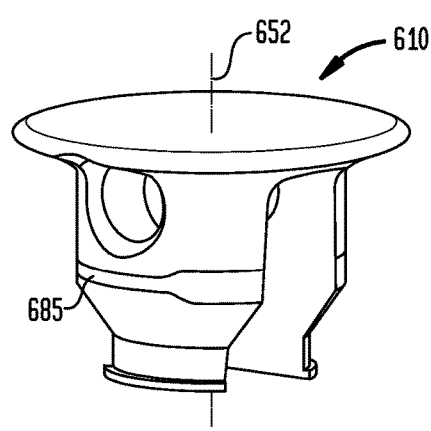
FIG. 6A is a perspective view of another embodiment of a cable plug, wherein the cable plug has an enlarged top surface and an interior conduit.
Figure 6B:
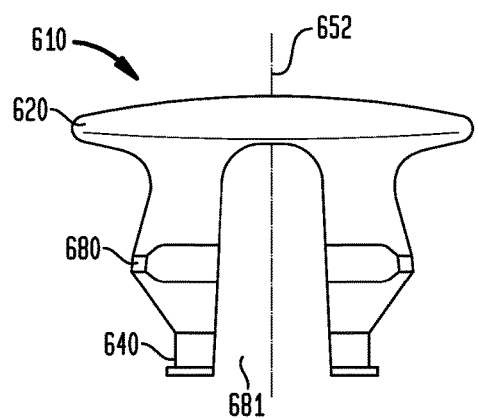
FIG. 6B is a profile view of the cable plug shown in FIG. 6A.
Figure 6C:
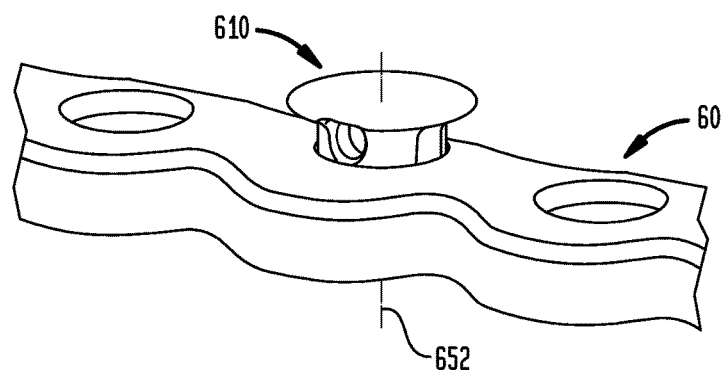
FIG. 6C is a perspective view of the cable plug shown in FIG. 6B, wherein the cable plug is engaged with an aperture in the bone plate.
Figure 6D:
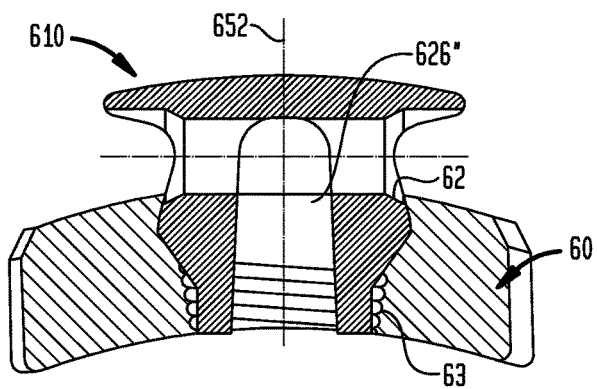
FIG. 6D is a cross-sectional view of the cable plug shown in FIG. 6A.
Figure 7A:
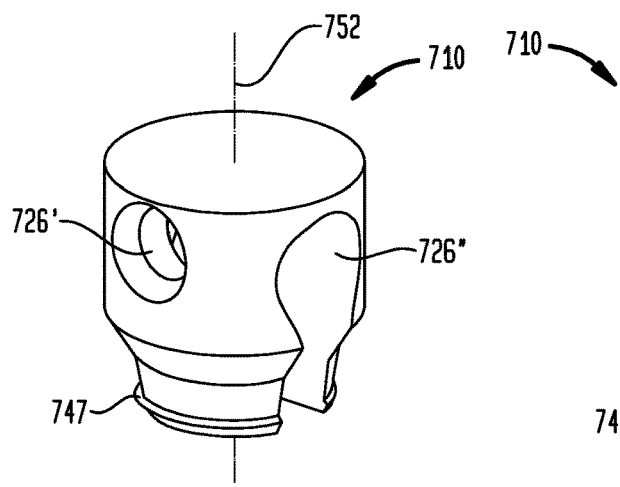
FIG. 7A is a perspective view of another embodiment of a cable plug, wherein the cable plug has an interior conduit in the form of a downward facing channel with a bulbous portion.
Figure 7B:
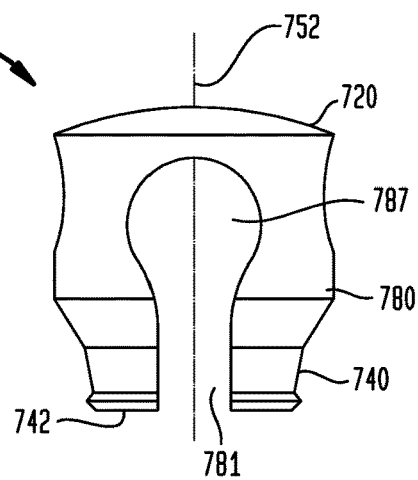
FIG. 7B is a profile view of the cable plug shown in FIG. 7A.
Figure 7C:
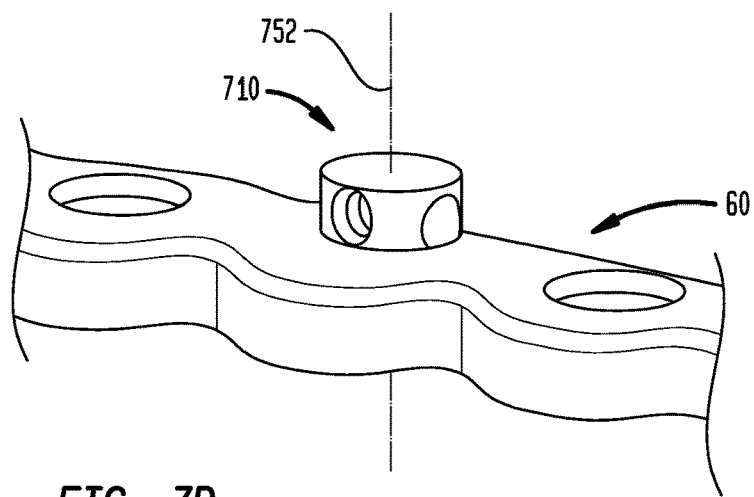
FIG. 7C is a perspective view of the cable plug shown in FIG. 7B, wherein the cable plug is engaged with an aperture in the bone plate.
Figure 7D:
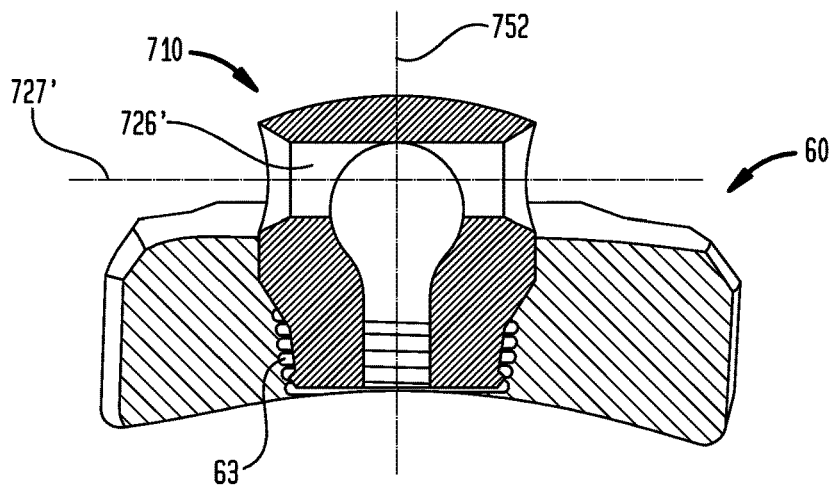
FIG. 7D is a cross-sectional view of the cable plug shown in FIG. 7A.
Figure 12A:
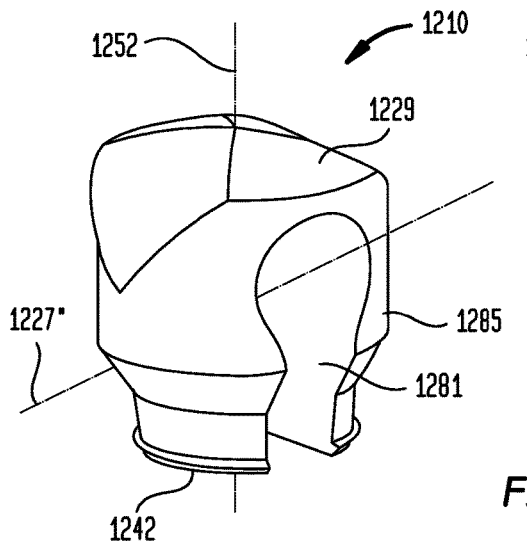
FIG. 12A is a perspective view of another embodiment of a cable plug, wherein the cable plug has a top surface of that is convexly shaped and an interior conduit in the form of a downward facing channel with a bulbous portion.
Figure 12B:
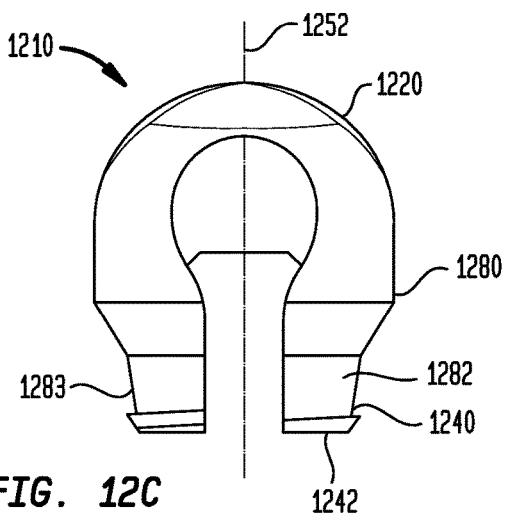
FIG. 12B is a profile view of the cable plug shown in FIG. 12A.
Figure 12C:
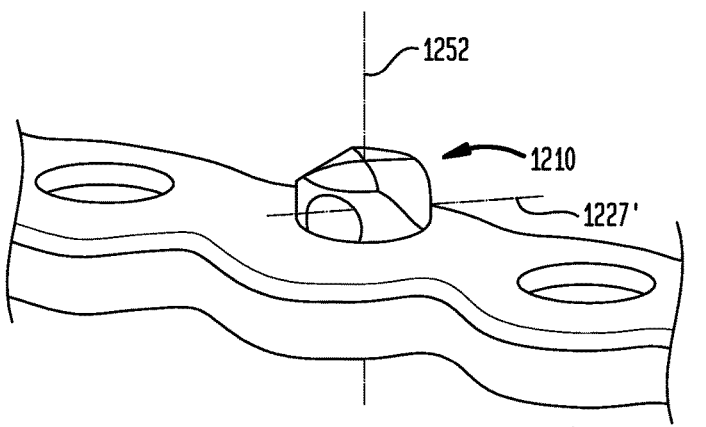
FIG. 12C is a perspective view of the cable plug shown in FIG. 12B, wherein the cable plug is engaged with an aperture in the bone plate.
Figure 12D:
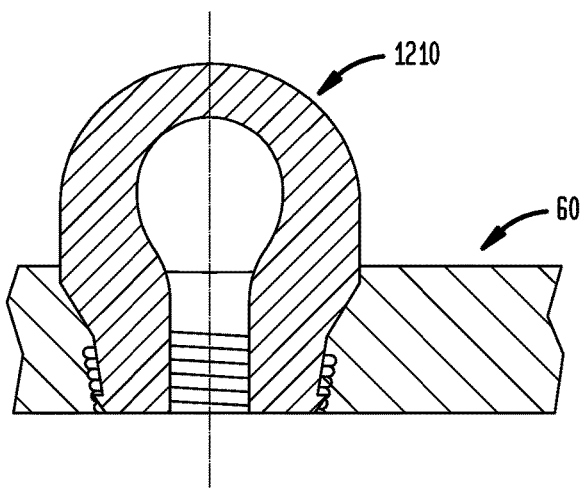
FIG. 12D is a cross-sectional view of the cable plug shown in FIG. 12A.

As shown in FIG. 2D, cable retaining portion 220 has an outer diameter less than or equal to an outer diameter of aperture 62 in bone plate 60. A top surface 229 of cable plug 210 is curved. Alternatively, this top surface may be flat, substantially flat, or any combination thereof. For example, a top surface 1229 of a cable plug 1210 is convexly shaped, as shown in FIG. 12A. In still other embodiments, a cable plug 1310 has a top surface 1329 that is curved to reduce the prominence of a cable retaining portion 1320 with respect to the exterior surface of bone plate 60, as in FIGS. 13A-D. Likewise, while top surface 229 is depicted as being smooth, any embodiment of this top surface may be dimpled, medicated, or have an otherwise variable finish. Still other variations of the cable retaining portion are contemplated. For example, as shown in FIGS. 3A-D, a cable plug 310 has a top surface 329 with an outer diameter larger than the outer diameter of aperture 62, thus giving a cable plug 310 a substantially "1" shaped profile. In still other embodiments, a top surface 429 of FIG. 4A is broken by a channel 426" extending along second lateral axis 427". Channel 426" desirably opens upwardly along a longitudinal axis 452 towards top surface 429. As noted below, each of the two cable retaining members forming channel 426" are intersected by an aperture 426'.

Cable retaining portion 220, and its counterparts, may incorporate a variety of cable receiving means. For example, cable retaining portion 220 of FIG. 2D has an aperture 226' extending along a first lateral axis 227'. Aperture 226' receives cable 61 within cable retaining portion 220. In FIG. 2D, aperture 226' has a substantially circular opening with beveled edges; although non-circular openings and varied edge treatments are possible. In FIG. 2D, first lateral axis 227' is substantially parallel with bottom surface 242 of cable plug 210. Alternatively, as shown in FIG. 12A, a first lateral axis 1227' may be angled with respect to a bottom surface 1242 of cable plug 1210 so as to receive cable wire 61 at a pre-determined angle therealong.

A plurality of cable retaining means may be also incorporated into cable retaining portion 220. For example, as noted above, FIGS. 4A-D depicts a channel 426" that extends along a second lateral axis 427" and is intersected by an aperture 426' extending along a first lateral axis 427'. As noted above, channel 426" desirably opens upwardly along a longitudinal axis 452 towards top surface 429. This enables the method step of wrapping cable wire 61 around the bone plate, through channel 426", and then through aperture 426' to secure cable wire 61 within cable retaining portion 420.

In FIGS. 5A-D, an aperture 526' of a cable plug 510 is intersected by or in communication with a portion of an interior conduit 581. Preferably, interior conduit 581 is defined by a pair of first and second sidewalls 582 and 583. In some embodiments, sidewalls 582 and 583 act as pair of first and second biased legs that form interior conduit 581. As illustrated, a passage 526" extends through cable plug 510 along a second lateral axis 527" to form at least a portion of conduit 581. Interior conduit 581 opens downwardly along a longitudinal axis 552 towards a fastening portion 540 of plug 510. The aperture described above may be omitted. For example, in FIGS. 13A-D, a cable plug 1310 has a passage 1326" that extends along a second lateral axis 1327" to form a portion of an interior conduit 1381. In contrast to above, passage 1326" serves as the only cable receiving means adapted to receive cable wire 61. The structure of plug 1310, and like embodiments, permits the method step of pushing cable plug 1310 into aperture 62 to receive a portion of cable wire 61 within passage 1326" of interior conduit 1381. Of course, the features of plug 1310 might alternatively be included within any embodiment of cable plug 110 described herein.

Figure 9A:
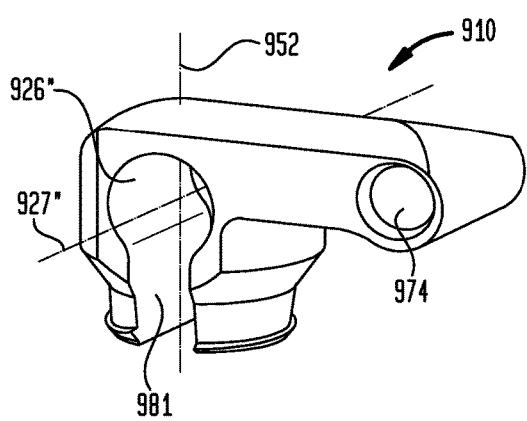
FIG. 9A is a perspective view of another embodiment of a cable plug that has a cable retaining arm with an aperture having a substantially circular opening.
Figure 9B:
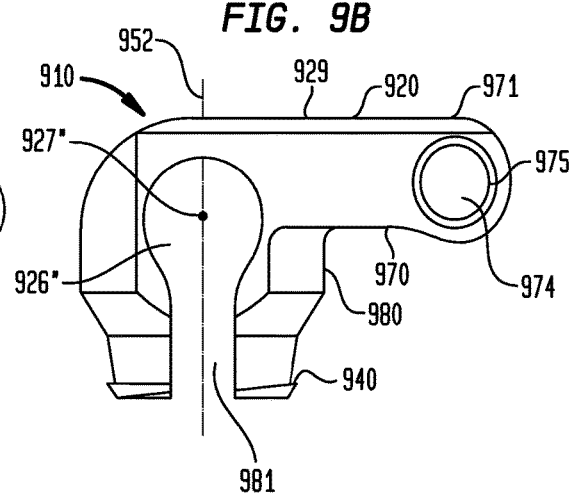
FIG. 9B is a profile view of the cable plug shown in FIG. 9A.
Figure 9C:
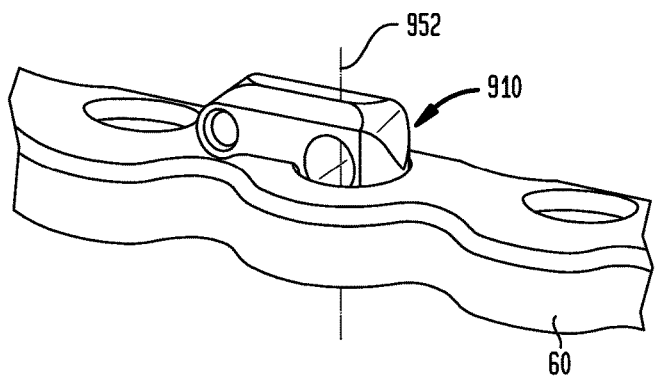
FIG. 9C is a perspective view of the cable plug shown in FIG. 9B, wherein the cable plug is engaged with an aperture in the bone plate.
Figure 9D:
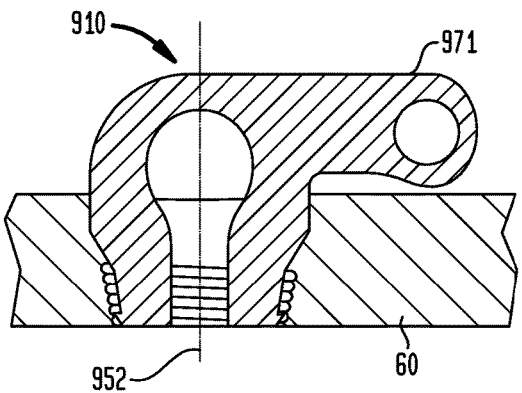
FIG. 9D is a cross-sectional view of the cable plug shown in FIG. 9A.
Figure 10A:
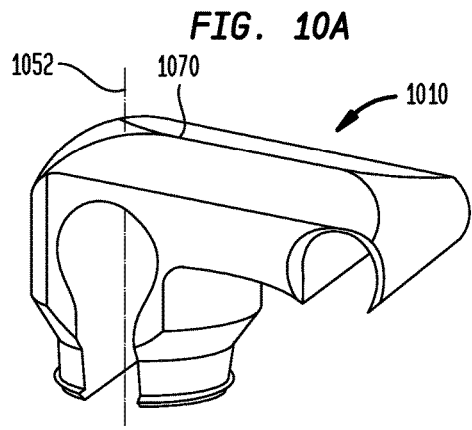
FIG. 10A is a perspective view of another embodiment of a cable plug that has a cable retaining arm with an aperture having a semi-circular opening.
Figure 10B:
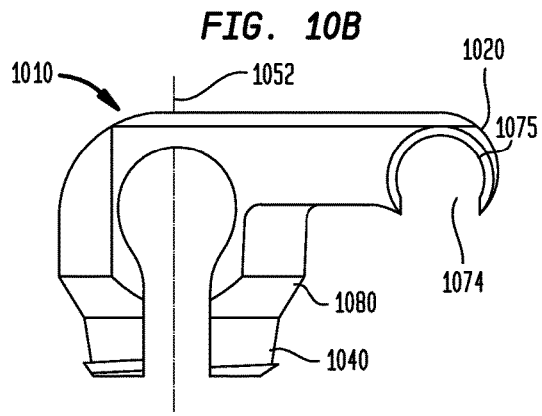
FIG. 10B is a profile view of the cable plug shown in FIG. 10A.
Figure 10C:
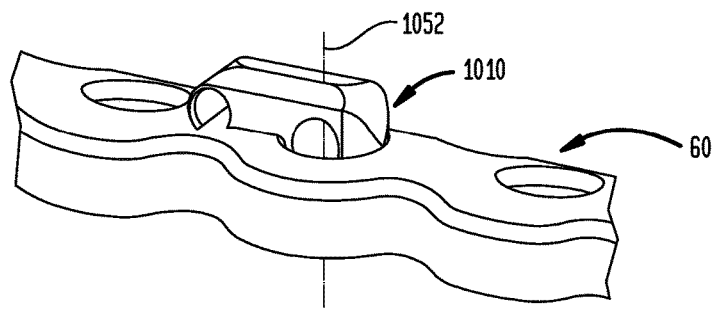
FIG. 10C is a perspective view of the cable plug shown in FIG. 10B, wherein the cable plug is engaged with an aperture in the bone plate.
Figure 10D:
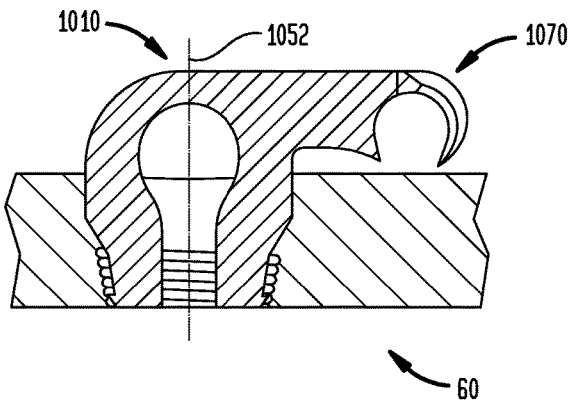
FIG. 10D is a cross-sectional view of the cable plug shown in FIG. 10A.

The cable retaining portion may also have one or more cable retaining arms extending outwardly therefrom. For example, FIGS. 9A-D show at least one cable retaining arm 970 extending from a surface of a cable retaining portion 920 of cable plug 910. As shown, each arm 970 has a top surface 971 contiguous with a top surface 929 of cable plug 910. A cable retaining means such as aperture 974, for example, is attached to cable retaining portion 920. In FIG. 9B, aperture 974 is depicted as having a substantially circular opening. Alternatively, an aperture 1074 may be similar to aperture 974, except for having a semi-circular opening, as shown in FIG. 10B. Aperture 1074 may also be adapted to capture a portion of cable wire 61. For example, the open portion of aperture 1074 may be slightly less than the width of cable wire 61 so that wire 61 may be snapped into aperture 1074.

Figure 11A:
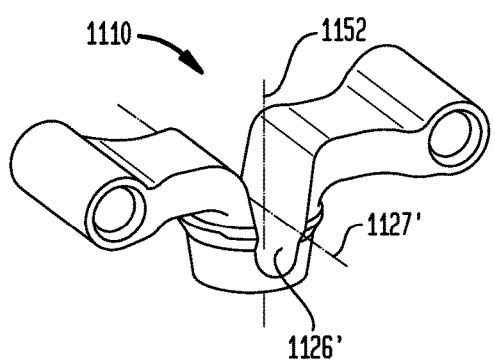
FIG. 11A is a perspective view of another embodiment of a cable plug, wherein the cable plug has a "V" shaped profile.
Figure 11B:
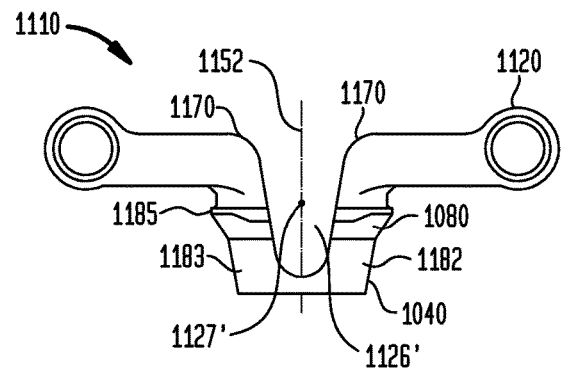
FIG. 11B is a profile view of the cable plug shown in FIG. 11A.
Figure 11C:
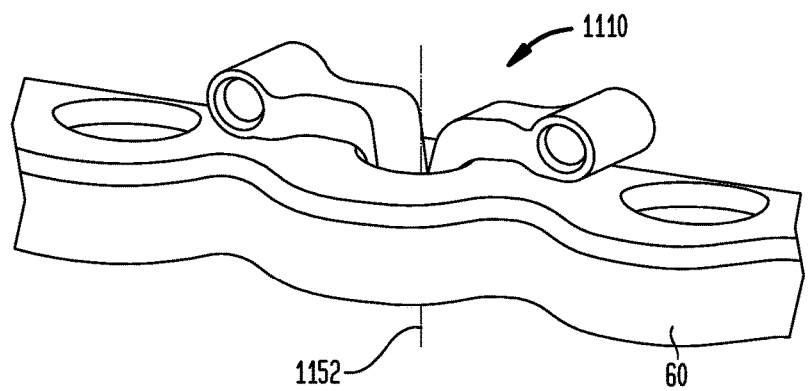
FIG. 11C is a perspective view of the cable plug shown in FIG. 11B, wherein the cable plug is engaged with an aperture in the bone plate.
Figure 11D:
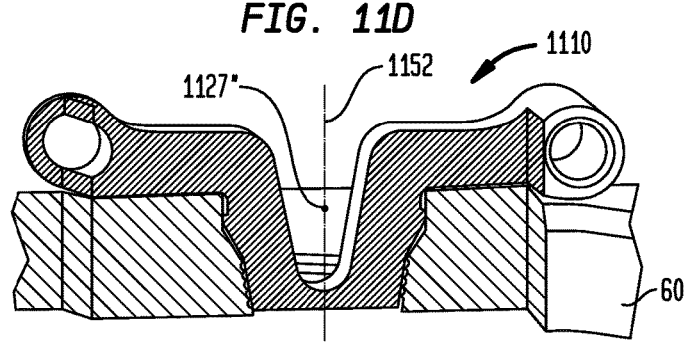
FIG. 11D is a cross-sectional view of the cable plug shown in FIG. 11A.

Still embodiments of the cable retaining portion are contemplated as being part of the present invention. For example, in FIGS. 11A-D, a cable retaining portion 1120 of a cable plug 1110 is divided by a channel 1126' along a first lateral axis 1127'. In contrast to above, channel 1126' opens upwardly along a longitudinal axis 1252 towards a cable retaining portion 1120. This configuration bestows plug 1110 with a "V" shaped profile. At least one cable retaining arm 1170 extends directly from either divided part of cable retaining portion 1120. Cable plug 1110 of FIGS. 11A-D may be engaged with aperture 62 in accordance with any engagement mode set forth herein. As shown in FIG. 11B, cable plug 1110 has two cable retaining arms 1170 extending therefrom, each having aperture for receiving wire 61. Plug 1110 might also comprise a plurality of cable retaining arms, wherein each arm 1170 is oriented transversely with respect to the other.

An exemplary embodiment of intermediate portion 280 is also depicted in FIGS. 2A-D, which depicts an interior conduit 281 extending along second lateral axis 227". Although the features of intermediate portion 280 are discussed in detail below, it should be noted that the dimensional variations between the respective portions of cable plug 210 may be slight. As a result, any reference to an intermediate portion in this application is made for convenience as any embodiment disclosed herein might alternatively be described as having these features without referencing an intermediate portion.

Any interior conduit described herein may be enclosed or open ended. In FIGS. 2A-D, interior conduit 281 is an enclosed conduit that is bounded along longitudinal axis 252 by cable retaining portion 220 and fastening portion 240; and bounded along first lateral axis 227' by a first sidewall 282 and a second sidewall 283. Each of first and second sidewalls 282 and 283 spans between cable retaining portion 220 and fastening portion 240 along longitudinal axis 252. The thickness and profile of sidewalls 282, 283, varies with respect to longitudinal axis 252. Preferably, the thickness of sidewalls 282, 283, is adapted to provide cable plug 210 with a desired range of flexural characteristics, as discussed further below. Interior conduit 281 is illustrated as having a substantially cylindrical opening, although the opening may have any geometric shape. Nonetheless, because interior conduit 281 has a substantially cylindrical opening, the interior profile of sidewalls 282, 283 is substantially curved. Of course, the shape of first and second sidewalls 282, 283 might also vary according to the profile of interior shape 281, the means for receiving cable member 61, the material composition of cable plug 210, or related attributes.

Conversely, interior conduit 1381 of cable plug 1310 is open ended. As shown in FIGS. 13A-13D, conduit 1381 is bounded along longitudinal axis 252 by cable retaining portion 1320 and bounded along a first lateral axis 1327' by a first sidewall 1382 and a second sidewall 1383 of an intermediate portion 1380. As noted above, each of sidewalls 1382 and 1383 may be a pair of first and second biased legs that form interior conduit 1381. A passage 1326" forms a portion of interior conduit 1381. As shown in FIG. 13A, the passage 1326" may form a bulbous profile 1387. In FIGS. 13A-D, passage 1326" has a chamfered entry portion, as noted below.

A variety of means for engaging a cable plug with a bone plate are contemplated as being part of the present invention. For example, first and second sidewalls 282 and 283 of cable plug 210 have a protrusion 285 extending outwardly therefrom. Preferably, protrusion 285 is adapted to engage at least a portion of aperture 62. Cable plug 210 may be inserted into aperture 62 of bone plate 60 so that protrusion 285 achieves an interference fit with the interior surfaces of aperture 62. For example, sidewalls 282 and 283 may be flexible so that protrusion 285 may be interference fit with aperture 62 when the width of protrusion 285 is slightly greater than the diameter of aperture 62. This allows cable plug 210 to be pushed into aperture 62 along longitudinal axis 252 until it is firmly wedged therein. Alternatively, at least a portion of cable plug 210, such as protrusion 285, may be composed of an elastically deformable material. For example, if aperture 62 contains threads 63, then protrusion 285 may be deformed into and between threads 63.

Still other modes of engagement are contemplated, for example, cable plug 210 may be rotatably engaged with aperture 62. As shown in FIGS. 6A-D, a protrusion 685 is adapted for receipt within at least one thread 63 of aperture 62. By virtue of this configuration, protrusion 685 may be screwed into aperture 62. This allows cable plug 610 to be engageable with bone plate 60 at a plurality of angles about longitudinal axis 652. Alternatively, as shown in FIGS. 11A-D, the width of a protrusion 1185 may be approximately equal to the maximum dimension of thread 63 so that protrusion 1185 may be pushed over and into thread 63. In this configuration, cable plug 1110 is engaged with aperture 62 when protrusion 1185 is snapped therein. While protrusion 285 is shown as being engageable with aperture 62 proximate to the top surface of bone plate 60, an equivalent protrusion might alternatively be engageable with aperture 62 at any point along longitudinal axis 252. Further still, as shown in FIG. 12A, a protrusion 1285 comprises a sloped portion of sidewalls 1282 and 1283 that does not extend outwardly therefrom.

As stated above, interior conduit 281 preferably has a cylindrical shaped opening that extends through intermediate portion 280 along second lateral axis 227". But of course, the opening of conduit 281 need not be substantially cylindrical or wholly contained within intermediate portion 280. For example, interior conduit 581 of FIGS. 5A-D forms a downward facing channel that extends through intermediate portion 580 and fastening portion 540 of cable plug 510. Yet, like interior conduit 281, interior conduit 581 is still formed between cable retaining portion 520, first and second sidewalls 582 and 583, and fastening portion 580. Preferably, a passage 526" forms at least a portion of the interior conduit, as noted above.

The various interior conduits described herein enable a number of important features. For example, because interior conduit 281 spans between cable retaining and fastening portions 220 and 240, the elements of intermediate portion 280, such as first and second sidewalls 282 and 283, may flex independently in response to any forces applied thereto by cable wire 61. This enables cable plug 210 to resiliently absorb many of the stress and strains that might otherwise cause fastening portion 240 to disengage from aperture 62 during implantation, or cause bone plate 60 to shift during use. As another example, because interior conduit 281 is in communication with aperture 226', portions of cable plug 210 may flex to engage aperture 62 of bone plate 60. In some embodiments, this allows cable plug 210 to simultaneously engage aperture 62 and receive cable wire 61.

Elements of cable plug 210 may be adapted to have varying degrees of biased resiliency. For example, because interior conduit 281 preferably has a cylindrical shape, cable plug 210 may be further adapted to bias first and second sidewalls 282, 283, against an interior surface of aperture 62 to further secure cable plug 210 therein. As another example, because the undivided parts of cable retaining portion 520 may function as a living hinge, cable plug 510 may be adapted to bias first and second sidewalls 582 and 583 outwardly against the inner surface of aperture 62. For cable plug 210, these biasing features may be greatly enhanced when the interior conduit 281 is in communication with aperture 226' because the additional void space allows cable plug 210 to have an expanded range of deformation. This biasing force may also be enhanced by the material composition of the cable plug, which may be comprised of an inherently resilient material. Alternatively, the structure of the interior conduit may be adapted to enhance the biasing force. For example, a cable plug 810 may have a passage 826" with a bulbous profile 887, as in FIG. 8B, that is adapted to enhance the biasing force.

Still other features are enabled by the interior conduit. For example, interior conduit 281 also reduces the frictional forces imposed on cable plug 210 during engagement with aperture 62 simply by reducing the surface area of first and second sidewalls 282, 283, and any portions of protrusion 285 extending outwardly therefrom. As another example, interior conduit 1281 of cable plug 1210 is depicted in FIGS.

12A-D as extending a second axis 1227" that is angled with respect to longitudinal axis 1252. As a result, cable plug 1210 may be adapted to receive cable wire 61 at a predetermined angle within aperture 62.

Each entrance to interior conduit 281 may be further modified to reduce the stresses imposed on cable wire 61. For example, an interior conduit 1381 of cable plug 1310 in FIGS. 13A-D has an entry portion 1384 that extends parallel to axis 1352. As shown, entry portion 1384 is chamfered to prevent cable wire 61 from bending around a hard corner when tightened. Desirably, this further reduces the cross-sectional area of plug 1310 to promote engagement of plug 1310 with aperture 62 of bone plate 60.

Numerous embodiments of fastening portion 140 are also disclosed herein. For example, each of FIGS. 2A-D depicts a fastening portion 240 having an outer circumference 243, a band 247, and a bottom surface 242. Band 247 preferably extends outwardly from outer circumference 243 to prevent cable plug 210 from lifting out of aperture 62. Similar to protrusion 285, band 247 is an exemplary fastening surface configured to engage at least a portion of aperture 62. For example, band 247 may obtain an interference fit with aperture 62. As another example, cable plug 210 may be snapped into aperture 62 when band 247 is pushed over and into thread 63. As yet another example, a cable plug 710 has a band 747 that may be rotatably engaged with aperture 62, as in FIGS. 7A-D.

To promote engagement with bone plate 60, band 247 of FIG. 2B, for example, has a curved fastening surface that is symmetrical about axis 252. This allows band 247 to slide over each thread 63 as cable plug 210 is inserted into aperture 62. Alternatively, as in FIG. 8B, a band 847 may be asymmetrical about axis 852. This allows at least a portion of band 847 to be a thread-like element that is angled to engage threads 63. Alternatively still, as in FIGS. 13A-D, a band 1347 may be an asymmetrical element that is divided into a first band element 1347A opposite of a second band element 1347B with respect to interior conduit 1381. As shown, this further secures cable plug 1310 in aperture 62 of bone plate 60 by permitting each of the band elements 1347A and 1347B to engage separate portions of thread 63. Band 747 may also be omitted. For example, fastening portion 1140 of FIGS. 11A-D is constructed without an equivalent band 747. Instead, cable plug 1110 is secured to bone plate 60 by protrusion 1185.

If the cable plug features a downward facing channel, like interior conduit 581 of cable plug 510, then either of the intermediate or fastening portions of the cable plug may be further adapted to receive a surgical wire 61, preferably within passage 526". As shown in FIGS. 13A-D, for example, a portion of interior conduit 1381 has a chamfered portion 1386 that chamfers away from axis 1352 and towards the outer surfaces of fastening portion 1340. Advantageously, this prevents cable wire 61 from being exposed to a hard corner and aids in capturing wire 61 in passage 1327". Of course, any embodiment of the interior conduit, such as conduit 281, may also be adapted to receive wire 61 therein.

Features of each cable plug disclosed above may also be incorporated into a cable collar or attachment plate in accordance with the present invention. Exemplary embodiments of the cable attachment plate are depicted in FIGS. 14-15 as plates 1410 and 1510. Wherever possible, if similar components to those of cable plug 110, 210, or other embodiment, are included in cable attachment plates 1410 or 1510, then similar reference numerals are utilized, but within that series of numbers. For example, cable attachment plate 1410, similar to cable plug 110, 210, 310, etc., also has a cable retaining portion 1420 integral with a fastening portion 1440. Each of the cable retaining and fastening portions 1420 and 1440 are disposed along a longitudinal axis 1452. Similar to above, each of these portions work in combination to reduce the potential shear stresses and strains that may be transferred to surgical cable 61 during implantation or use.

As shown in FIGS. 14A-E, a cable retaining portion 1420 of attachment plate 1410 has a first channel 1426' for receiving cable wire 61 along a portion of an axis 1427'. First channel 1426' is at least partially defined by at least two cable receiving members 1424 and 1425 that extend upwardly from a base surface of cable retaining portion 1420. Cable retaining portion 1420 also has a second channel 1426" extending therethrough along a second axis 1427" that is transverse with longitudinal axis 1452. This allows cable wire 61 to be wrapped through or out of second channel 1426", as needed, to secure bone plate 60 to bone 12. Advantageously, second channel 1426" allows cable wire 61 to be wrapped multiple times around bone 12 in a plurality of directions.

Second channel 1426" cuts through cable retaining members 1424, 1425 to form a resilient section 1423 of cable attachment plate 1410. Because it has a reduced cross-sectional area, resilient section 1423 may flex to place cable attachment plate 1410 in contact with bone plate 60. The rigidity, or inversely the flexibility, of resilient section 1423 is directly attributable to the material composition of plate 1410 and the cross-sectional area of resilient section 1423. Preferably, an interior perimeter 1428 surrounds resilient section 423 and a portion of second channel 1426". Perimeter 1428 is depicted as having rectangular shape, although any regular or irregularly shape is possible. Thus, even if the material composition of plate 1410 is rigid or semi-rigid, resilient section 1423 will remain flexible.

Figure 14A:
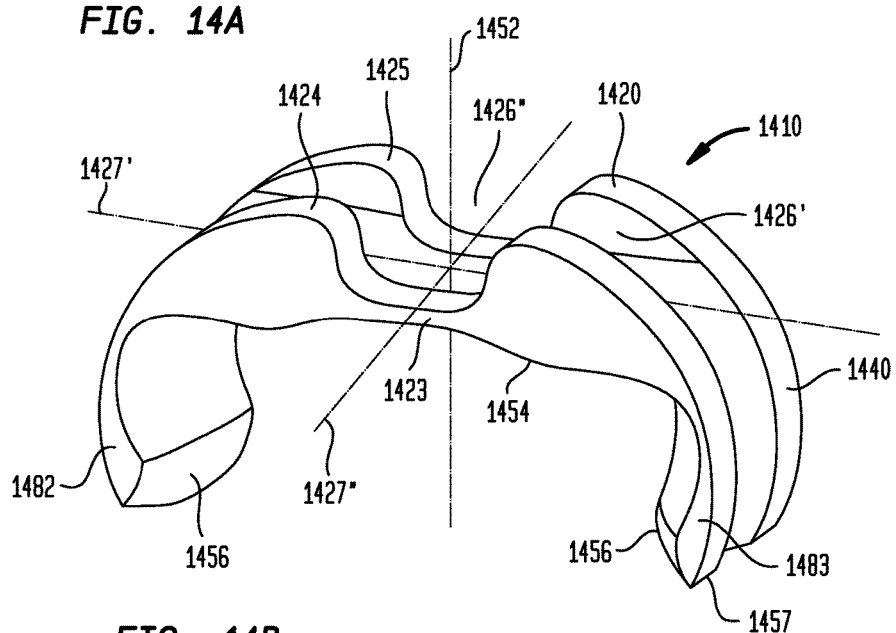
FIG. 14A is a perspective view of a cable attachment plate in accordance with the present invention.

Cable attachment plate 1410 also has a fastening portion 1440 disposed opposite of cable retaining portion 1420 along longitudinal axis 1452 of the plate 1410. As shown in FIG. 14A, fastening portion 1440 comprises a pair of first and second sidewalls 1482 and 1483 that are configured to move in a direction toward and a direction away from the longitudinal axis 1452. This movement preferably allows at least an interior portion of first and second sidewalls 1482, 1483 to contact an outer surface of bone plate 60 when cable attachment plate 1410 is operatively coupled to bone plate 60. For example, a portion of each first or second sidewall 1482, 1483 may be composed of an elastically deformable material adapted to flex, as needed, to ensure contact with the outer surface of bone plate 60. By virtue of this configuration, sidewalls 1482, 1483 may flex to accommodate the contours of any embodiment of bone plate 60.

Cable retaining portion 1420 and sidewalls 1482, 1483 form a bone plate contacting surface 1454. In FIG. 14D, for example, bone plate contacting surface 1454 is a continuous surface formed by the underside cable retaining portion 1420 and the interior surfaces of each of sidewalls 1482, 1483. Bone plate contact surface 1454 may be further adapted to engage the exterior surface of bone plate 60. For example, surface 1454 may be a smooth surface adapted to loosely grip the exterior surface of bone plate 60 so that its final position is influenced by the tightening of cable wire 61. Alternatively, surface 1454 may be undulating, intentionally roughened, or otherwise treated, to frictionally engage the exterior surface of bone plate 60.

As shown in FIG. 14D, bone plate contacting surface 1454 has at least one protrusion 1455 extending outwardly from surface 1454 to contact the outer surface of bone plate 60. Protrusion 1455 may be any known shape with any known surface treatment. For example, protrusion 1455 is shown as being pointed element in FIG. 14D; however, protrusion 1455 may also have a rounded surface, any portion of which may be further adapted to frictionally engage the exterior surface of bone plate 60. Bone plate contacting surface 1454 may also have a pair of first protrusions 1455A and 1455B opposite of a pair of second protrusions 1455C and 1455D, as shown, for example, in FIG. 14B. In this embodiment, each pair of protrusions, 1455A-D, is arranged to provide four distinct points of contact with bone plate 60. Each point of contact may be arranged about interior perimeter 1428 of cable retaining portion 1420 in a regular or irregular manner. For example, each point of contact is located proximate to a corner of interior perimeter 1428 in FIG. 14B and, thereby, arranged in regular manner about interior perimeter 1428. Alternatively, each contact may be irregularly arranged on bone plate contacting surface 1454 to promote four points of contact with the exterior surface of an irregularly shaped bone plate 60.

The points of contact provided by each embodiment of at least one protrusion 1455 disclosed herein also allow portions of cable attachment plate 1410 to conform to the exterior surface of bone plate 60. For example, interior perimeter 1428 may surround resilient section 1423 so that each protrusion 1455 serves as an integral fulcrum to distribute forces within plate 1410. This ensures that sidewalls 1482, 1483 will flex in a pre-determined manner. This configuration also allows each protrusion 1455 to transfer any compressive loads applied wire 61 during tightening, and yet also allows another portion of plate 1410, such as resilient section 1423 or sidewalls 1482, 1483, to flexibly conform to the exterior surface of bone plate 60.

To promote contact with bone plate 60, bone plate contact surface 1454 preferably has at least one contact anchor 1456 extending away from an end portion of at least one of sidewalls 1482, 1483 along first axis 1427'. Each contact anchor 1456 is preferably adapted to contact the exterior surface of bone plate 60. For example, each contact anchor 1456 on plate 1410 in FIGS. 14A-E has a triangular shape adapted for three point contact with the exterior surface of bone plate 60. Similar to above, any surface on contact anchor 1456 may be smooth or rough, like that of bone plate contacting surface 1454, or protrusions 1455, so as to promote contact with bone plate 60.

Figure 14B:
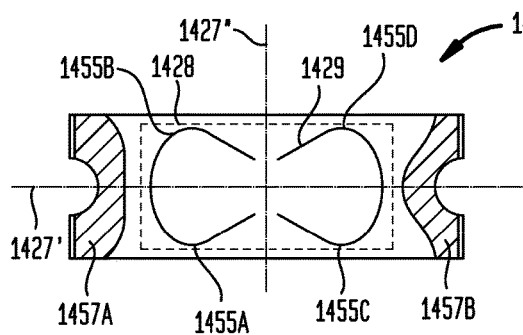
FIG. 14B is a cross-sectional view of the cable attachment plate shown in FIG. 14A.

As shown in FIG. 14B, the ends of first channel 1426' and each contact anchor 1456 combine to form a first cross-sectional area 1457A opposite of a second cross-sectional area 1457B. The varied shapes of cross-sectional area 1457A and 1457B facilitate placement of cable attachment plate 1410. For example, each of first and second cross-sectional areas 1457A and 1457B may be shaped to match the exact surface contours of bone plate 60. In this configuration, attachment plate 1410 may be placed in contact with bone plate 60 by sliding the interior surfaces of cross-sectional areas 1457A and 1457B along the exterior surface of bone plate 60 in a direction that is substantially parallel to axis 1452. Thus, if attachment plate 1410 is formed of a rigid material, such as metal, then plate 1410 can be slide into position along axis 1452. Areas 1457A and 1457B also allow plate 1410 to be rotated onto the bone plate about axis 1427'. For example, the rounded point of area 1457B may be placed against the exterior surface of the bone plate so that the planar area of 1457A can be rotated about second axis 1427" to be slid around and along the exterior surface of plate 60.

Each contact anchor 1456 is also adapted to facilitate removal of cable attachment plate 1410 from bone plate 60. In FIGS. 14A and 14D, for example, each contact anchor 1456 chamfers away from longitudinal axis 1452 to define a bottom edge 1457 of fastening portion 1440. This forms a space between bottom edge 1457 and the exterior surface of bone plate 60. Because of this space, a removal force may be applied to edge 1457 to de-couple attachment plate 1410 from bone plate 60 by prying one of sidewalls 1482 or 1483 away the exterior surface of plate 60.

Figure 14C:
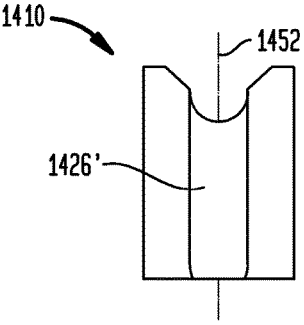
FIG. 14C is a side view of the cable attachment plate shown in FIG. 14A.
Figure 14D:
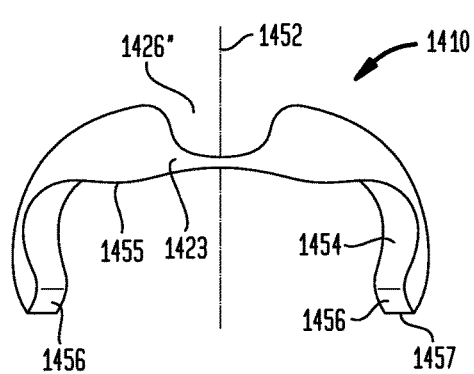
FIG. 14D is profile view of the cable attachment plate shown in FIG. 14A.
Figure 14E:
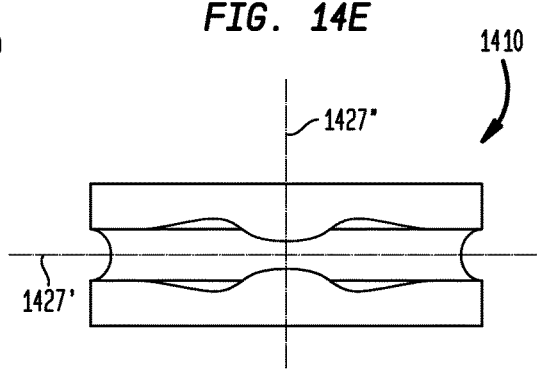
FIG. 14E is top view of the cable attachment plate shown in FIG. 14A.

In still other embodiments, elements of cable receiving members 1424, 1425 of cable retaining portion 1420 may be varied to provide various modes of securing cable wire 61 to bone plate 60. In FIG. 14C, for example, cable receiving members 1424 and 1425 are separated by a width along second axis 1427" that is equal to or greater than the diameter of cable wire 61. This allows cable wire 61 to move freely in and out of first channel 1426'. Alternatively, as shown in FIG. 14E, cable receiving members 1424 and 1425 are separated by a width along second axis 1427" that is slightly less than the diameter of cable wire 61. Thus, if only one of members 1424 or 1425 is flexible, then cable wire 61 may still be passed therebetween.

Figure 15A:
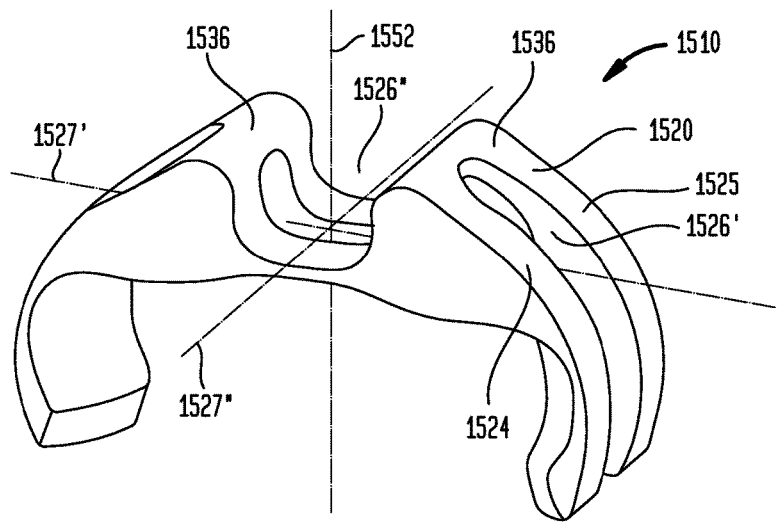
FIG. 15A is a perspective view of another embodiment of the cable attachment plate shown in FIG. 14A.
Figure 15B:
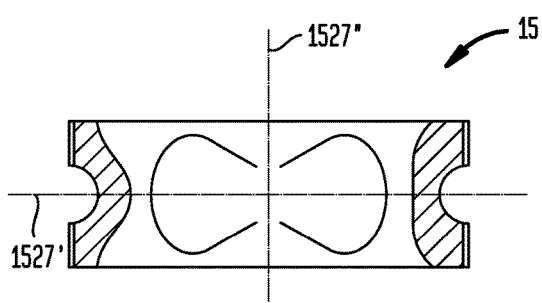
FIG. 15B is a cross-sectional view of the cable attachment plate shown in FIG. 15A.
Figure 15C:
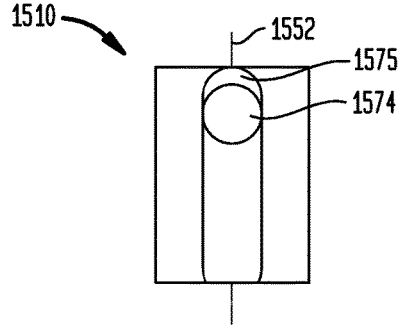
FIG. 15C is a side view of the cable attachment plate shown in FIG. 15A.
Figure 15D:
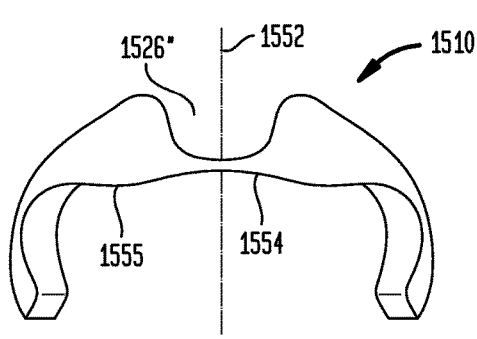
FIG. 15D is profile view of the cable attachment plate shown in FIG. 15A.
Figure 15E:
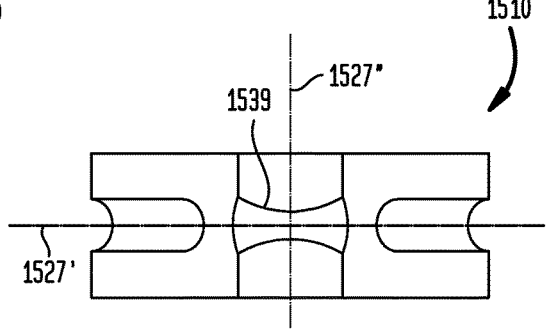
FIG. 15E is top view of the cable attachment plate shown in FIG. 15A.

As shown in FIGS. 15A-E, an alternate cable attachment plate 1510 may have a first channel 1526' that is at least partially enclosed. Preferably, as shown in FIG. 15A, plate 1510 has a pair of enclosed portions 1536. Each enclosed portion 1536 has an aperture 1574 that extends through a portion of cable attachment plate 1510. With reference to FIG. 15C, aperture 1574 is formed by spanning a cross member 1575 between each of cable receiving members 1524 and 1525 along second axis 1527". This allows cable wire 61 to be threaded through aperture 1574 as it is wrapped around bone plate 60. Like first channel 1426', first channel 1526' may have a width equal to or greater than the diameter of cable wire 61. Alternatively, as shown in FIG. 15E, at least a narrowed portion 1539 of first channel 1526' may be separated by a width that is slightly less than the width of cable wire 61 so that it may be secured therein in the manner described above.

Figure 16:
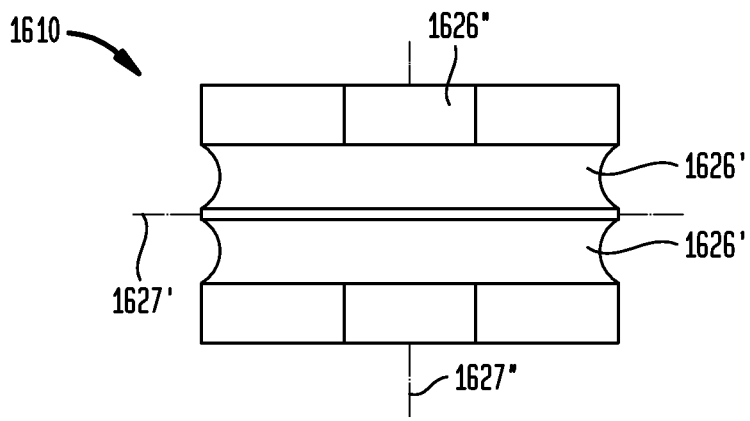
FIG. 16 is a top view of another cable attachment plate, wherein the plate has a plurality of channels.
Figure 17:
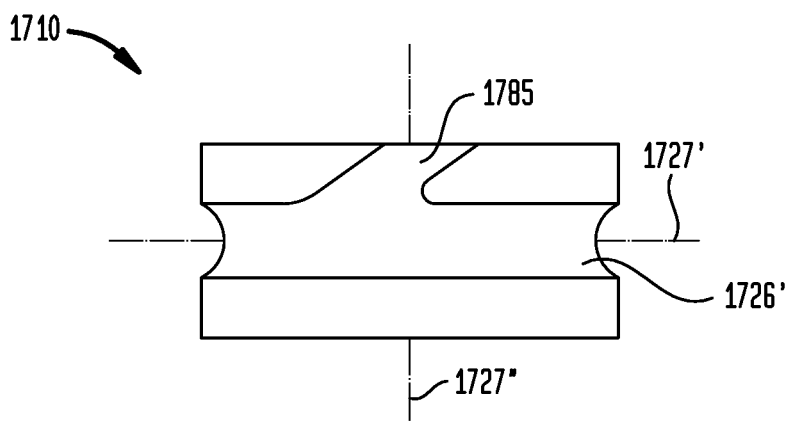
FIG. 17 is a top view of another cable attachment plate, wherein the plate has a redirecting feature.
Figure 18:
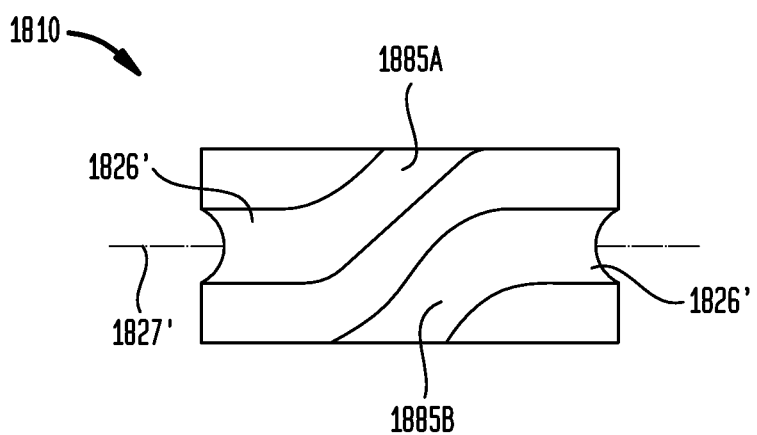
FIG. 18 is a top view of another cable attachment plate that has a plurality of redirecting features.

Other features of first channels 1426' or 1526' may also vary. For example, both of channels 1426' and 1526' are depicted in FIGS. 14A-15E as extending around cable retaining portion 1420 and fastening portion 1440 to form a continuous channel element that runs the length of attachment plate 1410. Alternatively, an exemplary embodiment of channel 1426' may only wrap around a portion of cable retaining portion 1420 or fastening portion 1440. As shown in FIG. 16, a plurality of first channels 1626' may also be incorporated into a plate 1610 so that wire 61 can be wrapped around bone plate 60 multiple times. Alternatively still, as shown in FIG. 17, a first channel 1726' may have a redirecting feature 1785 adapted to direct cable wire 61 out of a channel 1726' along at least one direction transverse to first axis 1727'. In still other embodiments, as in FIG. 18, a first channel 1826' may be bifurcated to have to two redirecting features 1885A and 1885B. This allows cable wire 61 to be wrapped in plate 1810 in a first direction and redirected out of plate 1810 in a second direction so that plate 1810 may be used to reverse the course of wire 61 as it is wrapped around bone plate 60.

Additional resilient features may also be added to cable retaining portion 1420. For example, the base surface of channel 1426' may be made from a resilient material, while each cable receiving member 1424 or 1425 is made of a rigid or semi-rigid material. This allows distinct portions of plate 1410 to change shape in response to compressive forces applied by tightening wire 61. Alternatively, an elongated spring-like element may be formed into the base surface along first axis 1427' to impart a desired resiliency into cable attachment plate 1410. Alternatively still, the elongated spring-like element may be used to enhance the biasing forces applied by plate 1410 to an exterior surface of bone plate 60. For example, the elongated spring-like element may be any resilient or biasing element that is imbedded in the base surface along a length parallel to bone plate contact surface 1454 so as to bias sidewalls 1482, 1483 towards or away from longitudinal axis 1452. Alternatively, the spring-like element may run the entire length of first channel 1426'.

Elements of fastening portion 1440 may also be modified. Sidewalls 1482 and 1483 may be biased, as noted above. For example, at least one sidewall may be biased to apply a compressive force against the exterior surface of bone plate 60. The biasing force may be imparted by the material composition and cross-section area of sidewalls 1482, 1483. Alternatively, the spring-like element described above may be embedded within sidewalls 1482 and 1483 at a location proximate to bone plate contact surface 1545 to impart the biasing force. Alternatively still, the biasing force may be imparted to sidewalls 1482, 1483 by resilient section 1423. As further shown in FIG. 14B, the underside of resilient section 1423 is formed or scored with a flexural feature 1429 adapted to ensure that sidewalls 1482, 1483 bend or flex in a pre-determined manner. This also ensures that first channel 1426' is rigid enough to withstand the forces applied by cable wire 61 as it is tightened, yet flexible enough to conform to any bone plate 60. Of course, the geometric configuration of flexural feature 1429 may vary.

Figure 19:
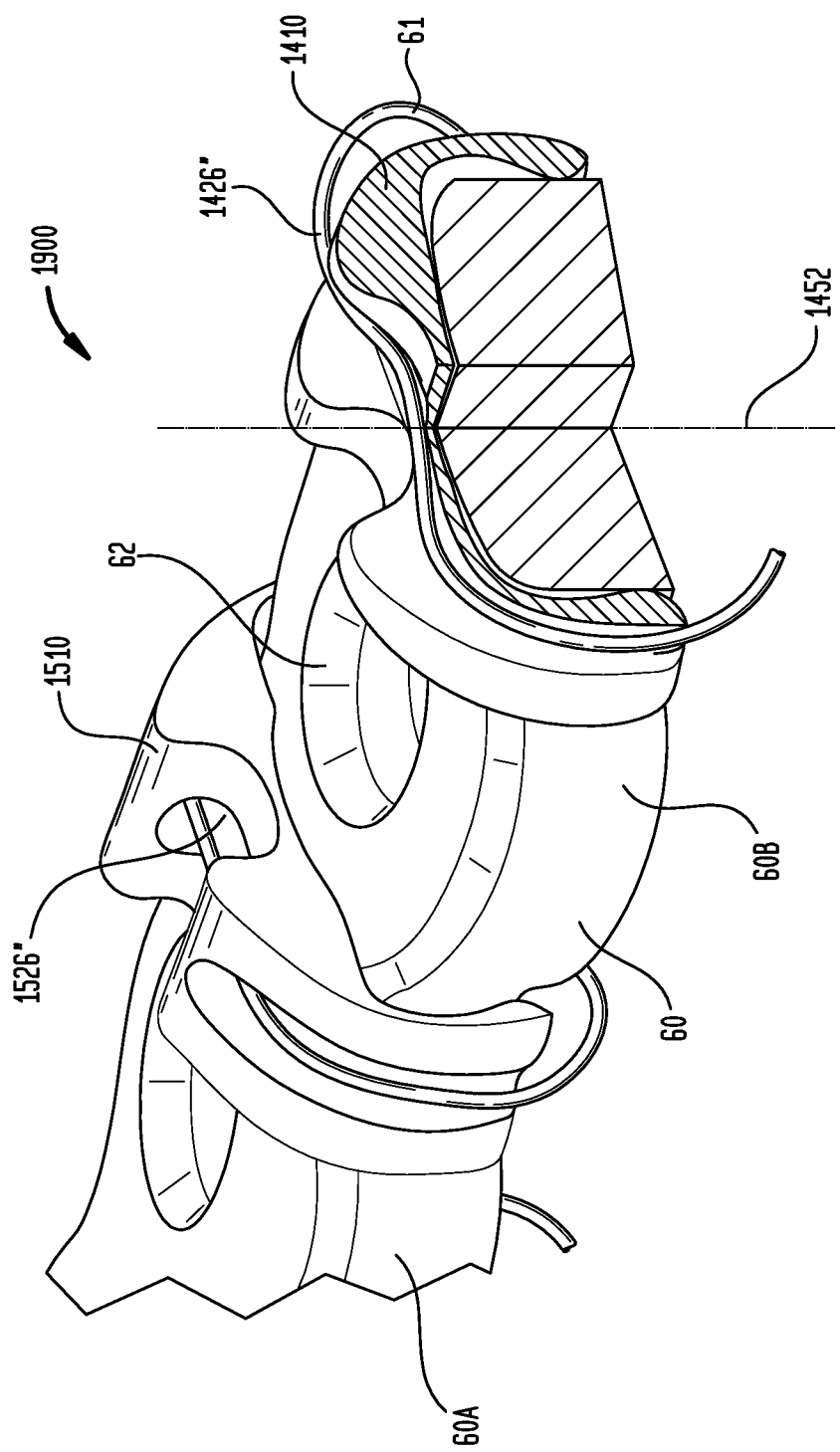
FIG. 19 is a perspective view of an exemplary system in accordance with the present invention.

Elements of plate 1410 and bone plate 60 may also be modified to promote contact with cable attachment plate 1410. The exterior surface of bone plate 60 may, for example, have at least one notch adapted to receive at least a portion of contact anchor 1456 therein. In this configuration, contact anchor 1456 is received in the notch to lock plate 1410 against bone plate 60. First and second sidewalls 1482 and 1483 may be biased to reinforce this locking mechanism. Alternatively still, anchor 1456 may have grasping portion that extends out from bone plate contacting surface 1454 to engage the underside of bone plate 60. Similar to above, this provides an alternate means of locking plate 1410 against bone plate 60. The perimeter of bone plate 60 may also vary. For example, bone plate 60 may have a rectangular shape, in which case, each contact anchor 1456 may have a cross section 1457 adapted to engage the relatively flat surfaces of a rectangular shaped bone plate 60. Alternatively, as shown in FIG. 19, bone plate 60 may have an undulating perimeter that defines at least two bulbous portions 60A and 60B. In this embodiment, each contact anchor 1456 may have a cross-section 1457 adapted for receipt between the exterior surfaces of bone plate 60 that are defined by the intersection of bulbous portions 60A and 60B. Advantageously, this allows each contact anchor 1456 to be wedged against the exterior surface of bone plate 60 when plate 1410 is mounted thereto.

A number of method steps are also contemplated as part of the present invention, each of which is enabled by the descriptions of each cable plug or cable attachment plate set forth above. A first exemplary method is enabled by FIGS. 4A-D. By virtue of the structure illustrated therein, this first method comprises the steps of: engaging cable plug 410 within aperture 62; wrapping a cable wire 61 around bone plate 60; and receiving wire 61 within at least one cable receiving means of cable 410 to secure bone plate 60 to bone 12. Preferably, the cable wire 61 is received within a first cable receiving means along first axis 427' and a second cable receiving means along second axis 427". Preferably still, receipt of the cable wire 61 in the second cable receiving means secures cable wire 61 within the first cable receiving means. In accordance with this method, the first cable receiving means may comprise channel 426', while the second cable receiving means comprises aperture 426". This exemplary method may further comprise the steps of: securing cable wire 61 within the first or second receiving means and tightening the surgical wire to cause cable plug 410 to engage with aperture 62. A final step may comprise fastening the cable wire 61 to itself or a portion of bone plate 60 to maintain a pre-determined tensile force within cable wire 61. Additional fastening hardware may also be included in this step.

A second exemplary method is enabled, for example, by FIGS. 5A-D. By virtue of the structure defined therein, this second embodiment comprises the steps of: wrapping a cable wire 61 around bone plate 60 so that a portion of cable wire 561 is adjacent to aperture 62; locating first sidewall 582 and second sidewall 583 of interior conduit 581 of cable plug 510 on either side of cable wire 61; and engaging fastening portion 540 with an interior surface of aperture 62. Engaging fastening portion 540 desirably causes cable wire 61 to be received within interior conduit 581. Preferably, cable plug 510 is secured within passage 526" when fastening portion 540 is engaged with aperture 62. Once received therein, cable wire 61 may contact an interior surface of interior conduit 581 located between sidewalls 582, 583. Advantageously, this method permits the application of a downward force onto cable retaining portion 520 of cable plug 510 to secure cable 61 to the bone plate 60 in a single step.

Methods of securing bone plate 60 to bone 12 using a cable attachment plate, like plates 1410 or 1510, are also disclosed. A first exemplary method is enabled, for example, by FIGS. 14A-E. This method comprises the step of placing bone plate contact surface 1454 of attachment plate 1410 in contact with bone plate 60. Bone plate 60 is then placed in contact with bone 12. Once plates 1410 and 60 are proximate to bone 12, then cable wire 61 may be received in at least first channel 1426' of cable retaining portion 1420 of plate 1410. Cable wire 61 is then wrapped around bone 12, bone plate 60, and cable attachment plate 1410, as needed, to secure bone plate 60 to bone 12. Once positioned, cable wire 61 is then tightened along its longitudinal axis to place at least a portion of the first and second sidewalls in contact with the exterior surface of bone plate 60 when the attachment plate 1410 is operatively coupled to bone plate 60. In a final step, cable wire 61 may be fastened, as noted above.

Any of these exemplary method stops may also be modified in accord with each embodiment of the cable attachment plates disclosed herein. As noted above, portions of sidewalls 1482, 1483, such as contact anchor 1456, may have a cross-sectional area 1457 adapted to match the contours of the exterior surface of bone plate 60. Thus, the step of placing contact surface 1454 adjacent bone plate 60 may include the step of sliding plate 1410 along axis 1452 until contact surface 1454 is adjacent plate 60. Alternatively, depending upon the rigidity of plate 1410, the placement step may include the step of placing contact anchor 1456A against the exterior surface of bone plate 60 and then rotating contact anchor 1456B into its contact position. For attachment plate 1510 of FIGS. 15A-E, the step of receiving cable wire 61 may further include the step of threading wire 61 through aperture 1574. Likewise, for plate 1610 of FIG. 16, the step of wrapping cable 61 may also include the step of receiving a portion of cable wire 61 in curved feature 1685 so as direct that portion of cable wire 61 out of attachment plate 1610. Further still, these method steps may further include the step of clamping cable wire 61 to itself, or to bone plate 60, to retain the tensile forces applied to wire 61.

Any combination of cable plugs and a cable attachment plates disclosed herein may also including a cable wire retention system in accordance with the present invention. Exemplary system components are illustrated include any elements depicted in FIGS. 1-20, although numerous additional systems might be equally described, in detail, based upon the structural descriptions within this disclosure For example, a system 1900 is depicted in FIG. 19 as including cable wire 61; bone plate 60, which has an exterior surface; an embodiment of an attachment plate 1410 (shown partially in section view); and an embodiment of attachment plate 1510. Of course, this exemplary system 1900 may include any embodiment of cable plug or cable wire attachment plate disclosed herein. For example, system 1900 may include at least one of any cable wire attachment plate 1410 or 1510, each having a cable retaining portion 1420 or 1520 and a fastening portion 1440 or 1540. In system 1900, the cable attachment plate may have at least one channel for receiving a cable wire therein, similar to first channels 1426' or 1526'. As before, the fastening portion may be disposed from the cable retaining portion about a longitudinal axis, such as axis 1452 or 1552, or their equivalents. Likewise, the fastening portion may have a pair of first and second sidewalls, like sidewalls 1482, 1483, that are configured to move in a direction toward and a direction away from the longitudinal axis 1452. Accordingly, system 1900 permits cable wire 61 to be secured to bone plate 60 by the attachment plate when the at least one protrusion is adjacent the exterior surface of the bone plate.

FIG. 20 depicts an alternate system 2000 in accordance with the present invention. As shown, this alternate system 2000 further comprises at least one cable plug 210, or other cable plug embodiment. In this system, a first portion of cable wire 61 is secured to bone plate 60 by cable attachment plate 1510, while a second portion of cable wire 61 is secured to bone plate 60 by cable plug 210. Advantageously, this allows one or more portions of cable wire 61 to be secured at multiple points along the length of bone plate 60. For example, system 2000 advantageously permits bone plate 60 to be secured to bone 12 by cable wire 61 at various points along the longitudinal axis of femur bone 12.

The cable retaining portion of any cable attachment plate in either of systems 1900 or 2000 may be adapted to secure cable wire 61 to bone plate 60 by any means described above. For example, the at least two cable receiving members 1424 and 1425 that form first channel 1426' may be separated by a width equal to or greater than the diameter of cable wire to facilitate the tightening of cable wire 61. Cable receiving members 1424, 1425 may be adapted to secure a portion of cable 61 therebetween. Cable wire 61 may also be threaded through an enclosed portion, such as aperture 1574 of plate 1510. In some embodiments, cable wire 61 is wrapped around the various elements of this system 2000 in a first direction and then redirected by the cable attachment plate. For example, cable wire 61 may be redirected to engage cable plug 210 disposed remotely therefrom along a longitudinal axis of bone plate 60. Cable wire 61 may be wrapped in the first direction to encircle an end plate embodiment of the cable attachment plate, such as plate 1710 in FIG. 16B, and then redirected by feature 1785 in a second direction opposite of the first direction. Advantageously, either of these configurations allows the opposing ends of wire 61 to be fastened proximate to a common end of bone plate 60.

It should further be appreciated than any combination of cable wires, cable plugs, cable attachment plates, bone plates, or related hardware, may also be arranged to define a cable fixation kit. For example, such a kit may comprise one or more fixed lengths of cable wire 61, a bone plate 60 adapted for contact with bone 12, at least one cable plug, such as plug 210, and at least one cable attachment plate, such as plate 1410. Additional fixation elements, such as bone screws, cable clamps, or like hardware, may also be included in the invented kit. To simplify delivery, each element of this kit may be secured in a container. Likewise, to promote sterilization, the entire kit and its contents may be autoclavable or otherwise adapted for sterilization using any known methods.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described by the appended claims.

The invention claimed is:

1. A cable plug having a body extending along a longitudinal axis from a first end to a second end, the cable plug comprising:
    a cable retaining portion provided adjacent the first end of the body and defining at least one passage for receiving a cable wire therethrough, the at least one passage extending in a transverse direction relative to the longitudinal axis;
    an intermediate portion disposed from the cable retaining portion about the longitudinal axis of the cable plug, the intermediate portion being inwardly tapered from an end nearest the first end of the body to an end nearest the second end of the body, the intermediate portion having a first sidewall and a second sidewall opposite of the first sidewall; and
    a fastening portion disposed from the intermediate portion adjacent the second end of the body and about the longitudinal axis, the fastening portion having a protrusion extending outwardly from an outer surface for fastening the cable plug to a bone plate,
    wherein an interior conduit is formed between the first and second sidewalls of the intermediate portion and wherein the conduit extends completely through the body in the transverse direction from the at least one passage through the second end of the body.

2. The cable plug of claim 1, further comprising an aperture that extends through the cable retaining portion along a first lateral axis.

3. The cable plug of claim 2, wherein a portion of the aperture is in communication with the at least one passage.

4. The cable plug of claim 1, wherein at least a portion of the interior conduit is circumferentially enclosed by the fastening portion.

5. The cable plug of claim 4, wherein the interior conduit has an oblong shaped opening.

6. The cable plug of claim 5, wherein either the first or second sidewall is configured to flex in response to a force applied to the cable plug.

7. The cable plug of claim 1, wherein the cable retaining portion has a top surface with a first diameter and the intermediate portion has a side surface with a second diameter, the first diameter being larger than the second diameter.

8. The cable plug of claim 1, wherein a portion of a top surface of the cable retaining portion is convexly shaped.

9. A cable plug having a body extending along a longitudinal axis from a first end to a second end, the cable plug comprising:
a cable retaining portion provided adjacent the first end of the body having an outer surface and a maximum diameter, the cable retaining portion defining at least one passage for receiving a cable wire therethrough, the at least one passage extending in a transverse direction relative to the longitudinal axis; and
a fastening portion coupled to the cable retaining portion adjacent the second end of the body and about the longitudinal axis of the cable plug, the fastening portion having a first sidewall and a second sidewall opposite of the first sidewall and a protrusion extending outwardly from an outer surface for fastening the cable plug to a bone plate, the first and second sidewalls defining a maximum diameter smaller than the maximum diameter of the cable retaining portion,
wherein the first and second sidewalls define an interior conduit extending completely through the body in the transverse direction from the at least one passage through the second end of the body, wherein a portion of the outer surface of the cable retaining portion located between the at least one passage and the fastening portion is chamfered toward the interior conduit, and wherein the fastening portion is configured to be inserted through an aperture defined in a top surface of the bone plate and to be fastened to the bone plate such that a portion of the at least one passage of the cable retaining portion is positioned above the top surface of the bone plate.

10. The cable plug of claim 9, further comprising an aperture that extends through the cable retaining portion along a first lateral axis.

11. The cable plug of claim 10, wherein a portion of the interior conduit intersects the aperture.

12. The cable plug of claim 9, wherein each of the first and second sidewalls is biased away from the longitudinal axis.

13. The cable plug of claim 9, wherein the cable retaining portion has a top surface with a first diameter and a side surface with a second diameter, the first diameter being larger than the second diameter.

14. The cable plug of claim 9, wherein the at least one passage has a bulbous profile corresponding to the profile of the cable wire.

15. The cable plug of claim 9, further comprising at least one cable retaining arm extending outwardly from the cable retaining portion along a first lateral axis, the at least one cable retaining arm having an aperture for receiving a surgical cable therethrough.

16. The cable plug of claim 9, wherein a top surface of the cable retaining portion is convexly shaped.

17. A cable plug having a body extending along a longitudinal axis from a first end to a second end, the cable plug comprising:
a cable retaining portion defining at least one passage for receiving a cable wire therethrough, the at least one passage extending in a transverse direction relative to the longitudinal axis;
an intermediate portion disposed from the cable retaining portion about the longitudinal axis of the cable plug, the intermediate portion being inwardly tapered from an end nearest the first end of the body to an end nearest the second end of the body; and
a fastening portion coupled to the cable retaining portion adjacent the second end of the body and about the longitudinal axis of the cable plug, the fastening portion having first and second biased legs forming an interior conduit that extends completely through the body in the transverse direction from the at least one passage through the second end of the body, each of the first and second biased legs having a protrusion extending outwardly from an outer surface thereof,
wherein the fastening portion is configured to be inserted through an aperture defined in a top surface of a bone plate to fasten the cable plug to the bone plate without extending past a bottom surface of the bone plate.

18. The cable plug of claim 17, wherein the protrusion of each of the first and second biased legs forms a portion of a thread.

19. The cable plug of claim 17, wherein each of the first and second biased legs has an inner sidewall opposite the outer surfaces thereof.

20. The cable plug of claim 19, wherein a length separates the inner sidewalls of the first and second biased legs, the length being less than a diameter of the at least one passage.

* * * * *